(12) United States Patent
Giese

(10) Patent No.: US 6,468,790 B1
(45) Date of Patent: Oct. 22, 2002

(54) METASTATIC BREAST AND COLON CANCER REGULATED GENES

(75) Inventor: Klaus Giese, Berlin (DE)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/712,016

(22) Filed: Nov. 13, 2000

Related U.S. Application Data

(63) Continuation of application No. 09/417,615, filed on Oct. 13, 1999.
(60) Provisional application No. 60/104,351, filed on Oct. 15, 1998.

(51) Int. Cl.$^7$ .......................... C12N 15/63; C12N 5/00; C12N 1/21; C07H 21/04
(52) U.S. Cl. .............................. 435/320.1; 435/226.3; 435/325; 435/455; 536/23.1; 536/23.5; 536/24.31; 536/24.33
(58) Field of Search .............................. 536/23.1, 23.5, 536/24.31, 24.33; 435/320.1, 325

(56) References Cited

U.S. PATENT DOCUMENTS 6,013,782 A * 11/2000 Dedhar et al.

FOREIGN PATENT DOCUMENTS

WO WO99/64590 12/1999

OTHER PUBLICATIONS

Russo et al, "Reexpression of the original tumor pattern by a human breast carcinoma cell line (MCF–7) in sponge culture", Journal of the National Cancer Institute, 1976, vol. 56, pp. 279–282.*
Shafie et al, "Formation of metastasis by human breast carcinoma cells (MCF–7) in nude mice", Cancer letters, 1980, vol. 11, pp. 81–87.*
NCI–CGAP, Accession No. AA586628, Sep. 25, 1997.*
Hillier et al, Accession No. AA405884.*
Accession No. 094894.
Alberts et al., Molecular Biology of the Cell, 3$^{rd}$ Edition, p. 465, 1994.
Andreasen et al., "The Urokinase–Type Plasminogen Activator System In Cancer Metastasis: A Review," *Int. J. Cancer* 72: 1–22, 1997.
Bork, P., "Powers and pitfalls in sequence analysis . . . ," *Genome Research 10:* 398–400, 2000.
Bowie et al., "Deciphering the message in protein sequences . . . ," *Science 247:* 1306–1310, 1990.
Brinkley et al., "Variations In Cell Form And Cytoskeleton In Human Breast Cancer Carcinoma Cells In Vitro," *Cancer Research 40:* 3118–3129, 1980.
Burgess et al., "Possible dissociation of the heparin–binding and mitogenic activities . . . ," *J. of Cell Biol.* 111: 2129–2138, 1990.
Carmeci et al., "Identification of a Gene (GPR30) with Homology to the G–Protein–Coupled Receptor Superfamily Associated with Estrogen Receptor Expression in Breast Cancer," *Genomics 45:* 607–617, 1997.
Challier et al., "Differential Expression Of The ufo/axl Oncogene In Human Leukemia–Lymphoma Cell Lines," *Leukemia 10:* 781–787, 1996.
El–Tanani and Green, "Insulin/IGF–1 Modulation Of The Expression Of Two Estrogen–Induced Genes In MCF–7 Cells," *Molecular and Cellular Endocrinology 121:* 29–35, 1996.
El–Tanani and Green, "Interaction Between Estradiol And Growth Factors In The Regulation Of Specific Gene Expression In MCF–7 Human Breast Cancer Cells," *J. Steroid Biochem. Molec. Biol. 60*(5–6): 269–276, 1997.
Fu et al., "Translational regulation of human p53 gene expression," *EMBO 15:* 4392–4401, 1996.
Guarino et al., "Malignant Mixed Müllerian Tumor Of The Uterus. Features Favoring Its Origin From A Common Cell Clone And An Epithelial–To–Mesenchymal Transformation Mechanism Of Histogenesis," *Tumori 84:* 391–397, 1998.
Hirohashi, "Inactivation Of The E–Cadherin–Mediated Cell Adhesion System In Human Cancers," *American Journal Of Pathology 153*(2): 333–339, 1998.
Hudson, EMBL Database Accession No. G21051, Jun. 1, 1996.
Koike et al., "Invasive Potentials Of Gastric Carinoma Cell Lines: Role Of $\alpha_2$ and $\alpha_6$ Integrins In Invasion," *J. Cancer Res. Clin. Oncol. 123:* 310–316, 1997.
Lazar et al., "Transforming growth factor alpha: mutation of aspartic acid . . . ," *Mole. And Cell. Biol. 8:* 1247–1252, 1988.
MacGrogan and Bookstein, "Tumour Suppressor Genes In Prostate Cancer," *Seminars In Cancer Biology 8:* 11–19, 1997.
McClean and Hill, "Evidence of post–translational regulation of P–glycoprotein . . . ," *Eur. J. of Cancer 29A:* 2243–2248, 1993.

(List continued on next page.)

*Primary Examiner*—Anthony C. Caputa
*Assistant Examiner*—Karen A. Canella
(74) *Attorney, Agent, or Firm*—Jane E. R. Potter; Kimberlin L. Morley; Robert P. Blackburn

(57) ABSTRACT

Gene sequences as shown in SEQ ID NOS:1–85 have been found to be significantly associated with metastatic potential of cancer cells, especially breast and colon cancer cells. Methods are provided for determining the risk of metastasis of a tumor, which involve determining whether a tissue sample from a tumor expresses a polypeptide encoded by a gene as shown in SEQ ID NOS:1–85, or a substantial portion thereof.

9 Claims, No Drawings

OTHER PUBLICATIONS

Morikawa et al., "In Vivo Selection of Highly Metastatic Cells From Surgical Specimens Of Different Primary Human Colon Carcinomas Implanted Into Nude Mice," *Cancer Research 48:* 1943–1948, 1988.

Nagase et al., "Prediction of the coding sequences of unidentified human genes . . . ," *DNA Research 5:* 277–286, 1998.

Perez–Ordoñez and Rosai, "Follicular Dendritic Cell Tumor: Review Of The Entity," *Seminars In Diagnostic Pathology 15*(2): 144–154, 1998.

Prasad et al., "Identification Of Keratins 18, 19 And heat–Shock Protein 90β As Candidate Substrates Of Proteolysis During Ionizing Radiation–Induced Apoptosis Of Estrogen–Receptor Negative Breast Tumor Cells," *International Journal Of Oncology 13:* 757–764, 1998.

Radinsky et al., "Level and Function of Epidermal Growth Factor Receptor Predict the Metastatic Potential of Human Colon Carcinoma Cells," *Clinical Cancer Research 1:* 19–31, 1995.

Sager et al., *Advances In Experimental Medicine And Biology. Chemistry And Biology Of Serpins,* Church et al. (eds.), Plenum Press, New York, 1997, Chapter 8, "Maspin. A Tumor Supressing Serpin," pp. 77–88.

Schulz et al., "The Genomic Structure Of The Human UFO Receptor," *Oncogene 8:* 509–513, 1993.

Scotlandi et al., "Multidrug Resistance and Malignancy in Human Osteosarcoma," *Cancer Research 56:* 2434–2439, 1996.

Shantz and Pegg, "Translation regulation of ornithine decarboxylase . . . ," *Intl. J. of Biochem. And Cell Biol. 31:* 107–122, 1999.

Stokkel et al., "Pretreatment Serum Lactate Dehydrogenase As Additional Staging Parameter In Patients With Small–Cell Lung Carcinoma," *J. Cancer Res. Clin. Oncol. 124:* 215–219, 1998.

Sugahara et al., "Expression Of Biologically Active Fusion Genes Encoding The Common α Subunit And Either The CGβ or FSHβ Subunits: Role Of A Linker Sequence," *Molecular And Cellular Endocrinology 125:* 71–77, 1996.

Takahashi et al., "Expression Of The pS2 Gene In Human Gastric Cancer Cells Derived From Poorly Differentiated Adenocarcinoma," *FEBS 261*(2): 283–286, 1990.

\* cited by examiner

METASTATIC BREAST AND COLON CANCER REGULATED GENES

CROSS-REFERENCE TO RELATED APPLICATIONS

This application is a continuation of pending U.S. patent application Ser. No. 09/417,615 filed Oct. 13, 1999, which claims the benefit of Provisional Application No. 60/104,351 filed Oct. 15, 1998, which are incorporated by reference herein in their entirety.

TECHNICAL FIELD OF THE INVENTION

This invention relates to methods for predicting the behavior of tumors. More particularly, the invention relates to methods in which a tumor sample is examined for expression of a specified gene sequence thereby to indicate propensity for metastatic spread.

BACKGROUND OF THE INVENTION

Breast cancer is one of the most common malignant diseases in women, with about 1,000,000 new cases per year worldwide. Colon cancer is another of the most common cancers. Despite use of a number of histochemical, genetic, and immunological markers, clinicians still have a difficult time predicting which tumors will metastasize to other organs. Some patients are in need of adjuvant therapy to prevent recurrence and metastasis and others are not. However, distinguishing between these subpopulations of patients is not straightforward, and course of treatment is not easily charted. There is a need in the art for new markers for distinguishing between tumors which will or have metastasized and those which are less likely to metastasize

SUMMARY OF THE INVENTION

It is an object of the present invention to provide markers for distinguishing between tumors which will or have metastasized and those which are less likely to metastasize. These and other objects of the invention are provided by one or more of the embodiments described below.

One embodiment of the invention provides an isolated and purified human protein having an amino acid sequence which is at least 85% identical to an amino acid sequence encoded by a nucleotide sequence selected from the group consisting of SEQ ID NOS:1–63 or the complement thereof.

Another embodiment of the invention provides a fusion protein which comprises a first protein segment and a second protein segment fused to each other by means of a peptide bond. The first protein segment consists of at least six contiguous amino acids selected from an amino acid sequence encoded by a nucleotide sequence selected from the group consisting of SEQ ID NOS:1–63 or the complement thereof.

Yet another embodiment of the invention provides an isolated and purified polypeptide consisting of at least six contiguous amino acids of a human protein having an amino acid sequence encoded by a nucleotide sequence selected from the group consisting of SEQ ID NOS:1–63 or the complement thereof.

Still another embodiment of the invention provides a preparation of antibodies which specifically bind to a human protein which comprises an amino acid sequence encoded by a nucleotide sequence selected from the group consisting of SEQ ID NOS:1–63 or the complement thereof.

Even another embodiment of the invention provides an isolated and purified subgenomic polynucleotide comprising at least 11 contiguous nucleotides of a nucleotide sequence which is at least 96% identical to a nucleotide sequence selected from the group consisting of SEQ ID NOS:1–63 or the complement thereof.

Another embodiment of the invention provides an isolated and purified gene which comprises a coding sequence comprising a nucleotide sequence selected from the group consisting of SEQ ID NOS:1–63 or the complement thereof.

Yet another embodiment of the invention provides a method for determining metastasis in a tissue sample. An expression product of a gene which comprises a coding sequence selected from the group consisting of SEQ ID NOS:1, 2, 4, 5, 9, 11, 13, 14, 18, 19, 20, 22, 24, 26, 29, 30, 33, 35, 36, 38–41, 45, 48, 52, 55, 57, 58, 60, 63–66, 69–74, 76, 80, 82, and 83 is measured in a tissue sample. A tissue sample which expresses the product is categorized as metastatic.

Still another embodiment of the invention provides a method for determining metastasis in a tissue sample. An expression product of a gene which comprises a sequence selected from the group consisting of SEQ ID NOS:3, 7, 8, 10, 12, 15–17, 21, 23, 28, 31, 34, 37, 42–44,46, 47, 49–51, 53, 59, 61, 62, 67, 68, 75, 77–79, 81, 84, and 85 is measured in a tissue sample. A tissue sample which does not express the product is categorized as metastatic.

Even another embodiment of the invention provides a method for determining metastatic potential in a tissue sample. An expression product of a gene which comprises a sequence selected from the group consisting of SEQ ID NOS:1, 2, 4, 5, 9, 11, 13, 14, 18, 19, 20, 22, 24, 26, 29, 30, 33, 35, 36, 38–41, 45, 48, 52, 55, 57, 58, 60, 63–66, 69–74, 76, 80, 82, and 83 is measured in a tissue sample. A tissue sample which expresses the product is categorized as having metastatic potential.

A further embodiment of the invention provides a method for determining metastatic potential in a tissue sample. An expression product of a gene which comprises a sequence selected from the group consisting of SEQ ID NOS:3, 7, 8, 10, 12, 15–17, 21, 23, 28, 31, 34, 37, 42–44, 46, 47, 49–51, 53, 59, 61, 62, 67, 68, 75, 77–79, 81, 84, and 85 is measured in a tissue sample. A tissue sample which does not express the product is categorized as having metastatic potential.

Another embodiment of the invention provides a method of predicting the propensity for metastatic spread of a breast tumor preferentially to bone or lung. An expression product of a gene which comprises a sequence selected from the group consisting of SEQ ID NO:1, 5, 11, 18, 20, 22, 24, 30, 33, 35, 36, 38, 45, 52, 58, 65, 66, 70, 74, 76, and 80 is measured in a breast tumor sample. A breast tumor sample which expresses the product is categorized as having a propensity to metastasize to bone or lung.

Even another embodiment of the invention provides a method of predicting propensity for metastatic spread of a breast tumor preferentially to lung. An expression product of a gene which comprises a sequence selected from the group consisting of SEQ ID NOS:2, 4, 9, 13 14, 19, 26, 29, 39–41, 48, 55,–57, 60, 63, 64, 72, 73, 82, and 83 is measured in a breast tumor sample. A breast tumor sample which expresses the product is characterized as having a propensity to metastasize to lung.

Still another embodiment of the invention provides a method of predicting propensity for metastatic spread of a colon tumor. An expression product of a gene which comprises the nucleotide sequence shown in SEQ ID NO:56 is measured in a colon tumor sample. A colon tumor sample which expresses the product is characterized as having a low propensity to metastasize.

Even another embodiment of the invention provides a method for determining metastasis in a tissue sample. An expression product of a gene which comprises a coding sequence selected from the group consisting of SEQ ID NOS:3, 7, 8, 10, 12, 15–17, 21, 23, 25, 28, 31, 34, 37, 42–44, 46, 47, 49, 61, 62, 67, 68, 75, 77–79, 5 81, 84, and 85 is measured in a tissue sample. A tissue sample which expresses the product is categorized as non-metastatic.

Yet another embodiment of the invention provides a method for determining metastasis in a tissue sample. An expression product of a gene which comprises a coding sequence selected from the group consisting of SEQ ID NOS:3, 7, 8, 10, 12, 15–17, 21, 23.25, 28, 31, 34, 37, 42–44, 46, 47, 49, 61, 62, 67, 68, 75, 77–79, 81, 84, and 85 is measured in a tissue sample. A tissue sample which does not express the product is categorized as metastatic.

The invention thus provides the art with a number of genes and proteins, which can be used as markers of metastasis. These are useful for more rationally is prescribing the course of therapy for breast or colon cancer patients.

DETAILED DESCRIPTION

It is a discovery of the present invention that a number of genes are differentially expressed between metastatic cancer cells, especially cancer cells of the breast and colon, and non-metastatic cancer cells. These genes are metastatic marker genes. This information can be utilized to make diagnostic reagents specific for the expression products of the differentially expressed genes. It can also be used in diagnostic and prognostic methods which will help clinicians in planning appropriate treatment regimes for cancers, especially of the breast or colon.

Some of the polynucleotides disclosed herein represent novel genes which are differentially expressed between non-metastatic cancer cells and cancer cells which have a potential to metastasize. SEQ ID NOS:1–63 represent novel metastatic marker genes (Table 1). SEQ ID NOS:64–85 represent known genes which have been found to be differentially expressed in metastatic relative to non-metastatic cancer cells (Table 2). Some of the metastatic marker genes disclosed herein are expressed in metastatic cells relative to non-metastatic cells, particularly in breast cancer cells which metastasize to bone and lung (SEQ ID NOS:1, 5, 11, 18, 20, 22, 24, 30, 33, 35, 36, 38, 45, 52, 58, 65, 66, 70, 74, 76, and 80). One metastatic marker gene (SEQ ID NO:56) is expressed in non-metastatic breast cancer cells and in colon cancer cells with low metastatic potential. Other metastatic marker genes are expressed in metastatic cancer cells, particularly in breast cancer cells which metastasize only to lung (SEQ ID NOS:2, 4, 9, 13, 14, 19, 26, 29, 39–41, 48, 55, 57, 60, 63, 64, 72, 73, 82, and 83). Still other metastatic marker genes (SEQ ID NOS:3, 7, 8, 10, 12, 15–17, 21, 23, 28, 31, 34, 37, 42–44, 46, 47, 49, 61, 62, 67, 68, 75, 77–79, 81, 84, and 85) are expressed in cancer cells which do not typically metastasize, particularly in breast cancer cells. Identification of these relationships and markers permits the formulation of reagents and methods as further described below. Other metastatic marker genes, such as those which comprise a nucleotide sequence shown in SEQ ID NOS:6, 27, 32, and 54, can be used to identify cancerous tissue, particularly breast cancer tissue.

Sequences of metastatic marker genes are disclosed in SEQ ID NOS:1–85. Metastatic marker proteins can be made by expression of the disclosed polynucleotide molecules. Amino acid sequences encoded by novel polynucleotides of the invention can be predicted by running a translation program for each of three reading frames for a disclosed sequence and its complement. Complete polynucleotide sequences can be obtained by chromosome walking, screening of libraries for overlapping clones, 5' RACE, or other techniques well known in the art.

Reference to metastatic marker nucleotide or amino acid sequences includes variants which have similar expression patterns in metastatic relative to non-metastatic cells, as described below. Metastatic marker polypeptides can differ in length from full-length metastatic marker proteins and contain at least 6, 8, 10, 12, 15, 18, 20, 25, 30, 35, 40, 45, 50, 55, 60, 65, 70, 75, 80, 85, 90, 95, 100, 120, 140, 160, 180, or 200 or more contiguous amino acids of a metastatic marker protein.

Variants of marker proteins and polypeptides can also occur. Metastatic marker protein or polypeptide variants can be naturally or non-naturally occurring. Naturally occurring metastatic marker protein or polypeptide variants are found in humans or other species and comprise amino acid sequences which are substantially identical to the proteins encoded by genes corresponding to the nucleotide sequences shown in SEQ ID NOS:1–85 or their complements. Non-naturally occurring metastatic marker protein or polypeptide variants which retain substantially the same differential expression patterns in metastatic relative to non-metastatic cancer cells as naturally occurring metastatic marker protein or polypeptide variants are also included here. Preferably, naturally or non-naturally occurring metastatic marker protein or polypeptide variants have amino acid sequences which are at least 85%, 90%, or 95% identical to amino acid sequences encoded by the nucleotide sequences shown in SEQ to ID NOS:1–85. More preferably, the molecules are at least 98% or 99% identical. Percent sequence identity between a wild-type protein or polypeptide and a variant is determined by aligning the wild-type protein or polypeptide with the variant to obtain the greatest number of amino acid matches, as is known in the art, counting the number of amino acid matches between the wild-type and the variant, and dividing the total number of matches by the total number of amino acid residues of the wild-type sequence.

Preferably, amino acid changes in metastatic marker protein or polypeptide variants are conservative amino acid changes, i.e. substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting metastatic marker protein or polypeptide variant. Properties and functions of metastatic marker protein or polypeptide variants are of the same type as a metastatic marker protein or polypeptide comprising amino acid sequences encoded by the nucleotide sequences shown in SEQ ID NOS:1–85, although the properties and functions of variants can differ in degree. Whether an amino acid change results in a metastatic marker protein or polypeptide variant with the appropriate differential expression pattern can readily be determined. For example, nucleotide probes can be selected from the marker gene sequences disclosed herein and used to detect marker gene mRNA in Northern blots or in tissue sections, as is known in the art. Alternatively, antibodies which specifically bind to protein products of metastatic marker genes can be used to detect expression of metastatic marker proteins.

Metastatic marker variants include glycosylated forms, aggregative conjugates with other molecules, and covalent conjugates with unrelated chemical moieties. Metastatic marker variants also include allelic variants, species variants, and muteins. Truncations or deletions of regions which do not affect the differential expression of metastatic marker genes are also metastatic marker variants. Covalent variants can be prepared by linking functionalities to groups which are found in the amino acid chain or at the N- or C-terminal residue, as is known in the art.

Full-length metastatic marker proteins can be extracted, using standard biochemical methods, from metastatic marker protein-producing human cells, such as metastatic breast or colon cancer cells. An isolated and purified metastatic marker protein or polypeptide is separated from other compounds which normally associate with a metastatic marker protein or polypeptide in a cell, such as certain proteins, carbohydrates, lipids, or subcellular organelles. A preparation of isolated and purified metastatic marker proteins or polypeptides is at least 80% pure; preferably, the preparations are 90%, 95%, or 99% pure.

Metastatic marker proteins and polypeptides can also be produced by recombinant DNA methods or by synthetic chemical methods. For production of recombinant metastatic marker proteins or polypeptides, coding sequences selected from the nucleotide sequences shown in SEQ ID NOS:1–85, or variants of those sequences which encode metastatic marker proteins, can be expressed in known prokaryotic or eukaryotic expression systems (see below). Bacterial, yeast, insect, or mammalian expression systems can be used, as is known in the art.

Alternatively, synthetic chemical methods, such as solid phase peptide synthesis, can be used to synthesize a metastatic marker protein or polypeptide. General means for the production of peptides, analogs or derivatives are outlined in Chemistry and Biochemistry of Amino Acids, Peptides, and Proteins—A Survey of Recent Developments, Weinstein, B. ed., Marcell Dekker, Inc., publ., New York (1983). Moreover, substitution of D-amino acids for the normal L-stereoisomer can be carried out to increase the half-life of the molecule. Metastatic marker variants can be similarly produced.

Non-naturally occurring fusion proteins comprising at least 6, 8, 10, 12, 15, 18, 20, 25, 30, 35, 40, 50, 55, 60, 65, 70, 75, 80, 85, 90, 95, 100, 120, 140, 160, 180, or 200 or more contiguous metastatic marker amino acids can also be constructed. Human metastatic marker fusion proteins are useful for generating antibodies against metastatic marker amino acid sequences and for use in various assay systems. For example, metastatic marker fusion proteins can be used to identify proteins which interact with metastatic marker proteins and influence their functions. Physical methods, such as protein affinity chromatography, or library-based assays for protein-protein interactions, such as the yeast two-hybrid or phage display systems, can also be used for this purpose. Such methods are well known in the art and can also be used as drug screens.

A metastatic marker fusion protein comprises two protein segments fused together by means of a peptide bond. The first protein segment comprises at least 6, 8, 10, 12, 15, 18, 20, 25, 30, 35, 40, 50, 55, 60, 65, 70, 75, 80, 85, 90, 95, 100, 120, 140, 160, 180, or 200 or more contiguous amino acids of a metastatic marker protein. The amino acids can be selected from the amino acid sequences encoded by the nucleotide sequences shown in SEQ ID NOS:1–85 or from variants of those sequences, such as those described above. The first protein segment can also comprise a full-length metastatic marker protein.

The second protein segment can be a full-length protein or a protein fragment or polypeptide. The fusion protein can be labeled with a detectable marker, as is known in the art, such as a radioactive, fluorescent, chemiluminescent, or biotinylated marker. The second protein segment can be an enzyme which will generate a detectable product, such as β-galactosidase. The first protein segment can be N-terminal or C-terminal, as is convenient.

Techniques for making fusion proteins, either recombinantly or by covalently linking two protein segments, are also well known. Recombinant DNA methods can be used to prepare metastatic marker fusion proteins, for example, by making a DNA construct which comprises coding sequences selected from SEQ ID NOS:1–85 in proper reading frame with nucleotides encoding the second protein segment and expressing the DNA construct in a host cell, as described below.

Isolated and purified metastatic marker proteins, polypeptides, variants, or fusion proteins can be used as immunogens, to obtain preparations of antibodies which specifically bind to a metastatic marker protein. The antibodies can be used, inter alia, to detect wild-type metastatic marker proteins in human tissue and fractions thereof. The antibodies can also be used to detect the presence of mutations in metastatic marker genes which result in under- or over-expression of a metastatic marker protein or in expression of a metastatic marker protein with altered size or electrophoretic mobility.

Preparations of polyclonal or monoclonal antibodies can be made using standard methods. Single-chain antibodies can also be prepared. Single-chain antibodies which specifically bind to metastatic marker proteins, polypeptides, variants, or fusion proteins can be isolated, for example, from single-chain immunoglobulin display libraries, as is known in the art. The library is "panned" against metastatic marker protein amino acid sequences, and a number of single chain antibodies which bind with high-affinity to different epitopes of metastatic marker proteins can be isolated. Hayashi et al., 1995, *Gene* 160:129–30. Single-chain antibodies can also be constructed using a DNA amplification method, such as the polymerase chain reaction (PCR), using hybridoma cDNA as a template. Thirion et al., 1996, *Eur. J. Cancer Prev.* 5:507–11.

Single-chain antibodies can be mono- or bispecific, and can be bivalent or tetravalent. Construction of tetravalent, bispecific single-chain antibodies is taught in Coloma and Morrison, 1997, *Nat. Biotechnol.* 15:159–63. Construction of bivalent, bispecific single-chain antibodies is taught in Mallender and Voss, 1994, *J. Biol. Chem.* 269:199–206.

A nucleotide sequence encoding the single-chain antibody can be constructed using manual or automated nucleotide synthesis, cloned into DNA expression constructs using standard recombinant DNA methods, and introduced into cells which express the coding sequence, as described below. Alternatively, single-chain antibodies can be produced directly using, for example, filamentous phage technology. Verhaar et al., 1995, *Int. J. Cancer* 61:497–501; Nicholls et al., 1993, *J. Immunol. Meth.* 165:81–91.

Metastatic marker-specific antibodies specifically bind to epitopes present in a full-length metastatic marker protein having an amino acid sequence encoded by a nucleotide sequence shown in SEQ ID NOS:1–85, to metastatic marker polypeptides, or to metastatic marker variants, either alone or as part of a fusion protein. Preferably, metastatic marker epitopes are not present in other human proteins. Typically, at least 6, 8, 10, or 12 contiguous amino acids are required to form an epitope. However, epitopes which involve non-contiguous amino acids may require more, e.g., at least 15, 25, or 50 amino acids.

Antibodies which specifically bind to metastatic marker proteins, polypeptides, fusion proteins, or variants provide a detection signal at least 5-, 10-, or 20-fold higher than a detection signal provided with other proteins when used in Western blots or other immunochemical assays. Preferably, antibodies which specifically bind to metastatic marker epitopes do not detect other proteins in immunochemical assays and can immunoprecipitate a metastatic marker protein, polypeptide, fusion protein, or variant from solution.

Antibodies can be purified by methods well known in the art. Preferably, the antibodies are affinity purified, by passing the antibodies over a column to which a metastatic marker protein, polypeptide, variant, or fusion protein is bound. The bound antibodies can then be eluted from the column, for example, using a buffer with a high salt concentration.

Subgenomic polynucleotides contain less than a whole chromosome. Preferably, the polynucleotides are intron-free. In a preferred embodiment, the polynucleotide molecules comprise a contiguous sequence of 10, 11, 12, 15, 20, 25, 30, 32, 35, 40, 45, 50, 60, 70, 74, 80, 90, 100, 125, 150, 154, 175, 182, 200, 243, or 268 nucleotides selected from SEQ ID NOS:1–85 or the complements thereof. The complement of a nucleotide sequence shown in SEQ ID NOS:1–85 is a contiguous nucleotide sequence which forms Watson-Crick base pairs with a contiguous nucleotide sequence shown in SEQ ID NOS:1–85. The complement of a nucleotide sequence shown in SEQ ID NOS:1–85 (the antisense strand) is also a subgenomic polynucleotide, and can be used provide marker protein antisense oligonucleotides. Double-stranded polynucleotides which comprise one of the nucleotide sequences shown in SEQ ID NOS:1–85 are also subgenomic polynucleotides. Metastatic, marker protein subgenomic polynucleotides also include polynucleotides which encode metastatic marker protein-specific single-chain antibodies and ribozymes, or fusion proteins comprising metastatic marker protein amino acid sequences.

Degenerate nucleotide sequences encoding amino acid sequences of metastatic marker protein and or variants, as well as homologous nucleotide sequences which are at least 85%, 90%, 95%, 98%, or 99% identical to the nucleotide sequences shown in SEQ ID NOS:1–85, are also metastatic marker subgenomic polynucleotides. Typically, homologous metastatic marker subgenomic polynucleotide sequences can be confirmed by hybridization under stringent conditions, as is known in the art. Percent sequence identity between wild-type and homologous variant sequences is determined by aligning the wild-type polynucleotide with the variant to obtain the greatest number of nucleotide matches, as is known in the art, counting the number of nucleotide matches between the wild-type and the variant, and dividing the total number of matches by the total number of nucleotides of the wild-type sequence. A preferred algorithm for calculating percent identity is the Smith-Waterman homology search algorithm as implemented in MPSRCH program (Oxford Molecular) using an affine gap search with the following search parameters: gap open penalty of 10, and gap extension penalty of 1.

Metastatic marker subgenomic polynucleotides can be isolated and purified free from other nucleotide sequences using standard nucleic acid purification techniques. For example, restriction enzymes and probes can be used to isolate polynucleotide fragments which comprise nucleotide sequences encoding a metastatic marker protein. Isolated and purified subgenomic polynucleotides are in preparations which are free or at least 90% free of other molecules.

Complementary DNA molecules which encode metastatic marker proteins can be made using reverse transcriptase, with metastatic marker mRNA as a template. The polymerase chain reaction (PCR) or other amplification techniques can be used to obtain metastatic marker subgenomic polynucleotides, using either human genomic DNA or cDNA as a template, as is known in the art. Alternatively, synthetic chemistry techniques can be used to synthesize metastatic marker subgenomic polynucleotides which comprise coding sequences for regions of metastatic marker proteins, single-chain antibodies, or ribozymes, or which comprise antisense oligonucleotides. The degeneracy of the genetic code allows alternate nucleotide sequences to be synthesized which will encode a metastatic marker protein comprising amino acid sequences encoded by the nucleotide sequences shown in SEQ ID NOS:1–85.

Purified and isolated metastatic marker subgenomic polynucleotides can be used as primers to obtain additional copies of the polynucleotides or as probes for identifying wild-type and mutant metastatic marker protein coding sequences. Metastatic marker subgenomic polynucleotides can be used to express metastatic marker mRNA, protein, polypeptides, or fusion proteins and to generate metastatic marker antisense oligonucleotides and ribozymes.

A metastatic marker subgenomic polynucleotide comprising metastatic marker protein coding sequences can be used in an expression construct. Preferably, the metastatic marker subgenomic polynucleotide is inserted into an expression plasmid (for example, the Ecdyson system, pIND, In Vitro Gene). Metastatic marker subgenomic polynucleotides can be propagated in vectors and cell lines using techniques well known in the art. Metastatic marker subgenomic polynucleotides can be on linear or circular molecules. They can be on autonomously replicating molecules or on molecules without replication sequences. They can be regulated by their own or by other regulatory sequences, as are known in the art.

A host cell comprising a metastatic marker expression construct can then be used to express all or a portion of a metastatic marker protein. Host cells comprising metastatic marker expression constructs can be prokaryotic or eukaryotic. A variety of host cells are available for use in bacterial, yeast, insect, and human expression systems and can be used to express or to propagate metastatic marker expression constructs (see below). Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

A metastatic marker expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the metastatic marker protein, variant, fusion protein, antibody, or ribozyme. The polynucleotide segment is located downstream from the promoter. Transcription of the polynucleotide segment initiates at the promoter. The expression construct can be linear or circular and can contain sequences, if desired, for autonomous replication.

Bacterial systems for expressing metastatic marker expression constructs include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Nat'l Acad. Sci. USA* (1983) 80: 21–25, and Siebenlist et al., *Cell* (1980) 20: 269.

Expression systems in yeast include those described in Hinnen et al., *Proc. Nat'l Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202 :302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. Nos. 4,837,148, 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Nat'l Acad. Sci. USA* (1984) 81: 1470–1474, Kelly and Hynes, *EMBO J.* (1985) 4: 475479; EP 244,234, and WO 91/00357.

Expression of metastatic marker expression constructs in insects can be carried out as described in U.S. Pat. No. 4,745,051, Friesen et al. (1986) "The Regulation of Baculovirus Gene Expression" in: The Molecular Biology of Baculoviruses (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Nat'l Acad. Sci. USA* (1985) 82: 8404, Miyajima at al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in Genetic Engineering (Setlow, J. K. et al. eds.), Vol. 8 (Plenum Publishing, 1986), pp. 277–279, and Maeda et al., *Nature*, (1985) 315: 592–594.

Mammalian expression of metastatic marker expression constructs can be achieved as described in Dijkema et al., *EMBO J.* (1985) 4: 761, Gorman et al., *Proc. Nat'l Acad. Sci. USA* (1982b) 79: 6777, Boshart et al., *Cell* (1985) 41: 521 and U.S. Pat. No. 4,399,216. Other features of mammalian expression of metastatic marker expression constructs can be facilitated as described in Ham and Wallace, *Meth. Enz.* (1979) 58: 44, Barnes and Sato, *Anal. Biochem.* (1980) 102: 255, U.S. Pat. Nos. 4,767,704, 4,657,866, 4,927,762, 4,560,655, WO 90/103430, WO 87/00195, and U.S. Pat. No. RE 30,985.

Subgenomic polynucleotides of the invention can also be used in gene delivery vehicles, for the purpose of delivering a metastatic marker mRNA or oligonucleotide (either with the sequence of native metastatic marker mRNA or its complement), full-length metastatic marker protein, metastatic marker fusion protein, metastatic marker polypeptide, or metastatic marker-specific ribozyme or single-chain antibody, into a cell preferably a eukaryotic cell. According to the present invention, a gene delivery vehicle can be, for example, naked plasmid DNA, a viral expression vector comprising a metastatic marker subgenomic polynucleotide, or a metastatic marker subgenomic polynucleotide in conjunction with a liposome or a condensing agent.

In one embodiment of the invention, the gene delivery vehicle comprises a promoter and a metastatic marker subgenomic polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

A metastatic marker gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the metastatic marker gene delivery vehicle is a recombinant retroviral vector. Recombinant retroviruses and various uses thereof have been described in numerous references including, for example, Mann et at., *Cell* 33:153, 1983, Cane and Mulligan, *Proc. Nat'l Acad. Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et at., *J. Neurosurg.* 79:729–735, 1993 (U.S. Pat. No. 4,777,127, GB 2,200,651, EP 0,345,242 and WO91/02805).

Particularly preferred retroviruses are derived from retroviruses which 15 include avian leukosis virus (ATCC Nos. VR-535 and VR-247), bovine leukemia virus (VR-1315), murine leukemia virus (MLV), mink-cell focus-inducing virus (Koch et al., *J. Vir.* 49:828, 1984; and Oliff et al., *J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Graffi (Ru et at, *J. Vir.* 67:4722, 1993; and Yantchev *Neoplasma* 26:397, 1979), Gross (ATCC No. VR-590), Kirsten (Albino et al., *J. Exp. Med.* 164:1710, 1986), Harvey sarcoma virus (Manly et al., *J. Vir.* 62:3540, 1988; and Albino et al., *J. Exp. Med.* 164:1710, 1986) and Rauscher (ATCC No. VR-998), and Moloney MLV (ATCC No. VR-190). A particularly preferred non-mouse retrovirus is Rous sarcoma virus. Preferred Rous sarcoma viruses include Bratislava (Manly et al., *J. Vir.* 62:3540, 1988; 30 and Albino et al., *J. Exp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g., ATCC Nos. VR-724, VR-725, VR-354) viruses.

Any of the above retroviruses can be readily utilized in order to assemble or construct retroviral metastatic marker gene delivery vehicles given the disclosure provided herein and standard recombinant techniques (e.g., Sambrook et al., *Molecular Cloning: A Laboratory Manual*, 2d ed., Cold Spring Harbor Laboratory Press, 1989, and Kunkle, *PNAS* 82:488, 1985) known in the art. Portions of retroviral Metastatic marker expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 07/800, 921, filed Nov. 29, 1999). Recombinant retroviruses can be produced which direct the site-specific integration of the recombinant retroviral genome into specific regions of the host cell DNA. Such site-specific integration can be mediated by a chimeric integrase incorporated into-the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, *Biotechniques* 6:616–627, 1988, and Rosenfeld et al., *Science* 252:431–434, 1991, WO 93/07283, WO 93/06223, and WO 93/07282).

A metastatic marker gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral metastatic marker gene delivery vehicles can also be constructed and used to deliver metastatic marker amino acids or nucleotides. The use of adeno-associated viral gene delivery vehicles in vitro is described in Chatterjee et al., *Science* 258: 1485–1488 (1992). Walsh et al., *Proc. Nat'l Acad. Sci.* 89: 7257–7261 (1992), Walsh et al., *J. Clin. Invest.* 94: 1440–1448 (1994), Flotte et al., *Biol. Chem.* 268: 3781–3790 (1993). Ponnazhagan et al., *J. Exp. Med.* 179: 733–738 (1994), Miller et al., *Proc. Nat'l Acad. Sci.* 91: 10183–10187 (1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al., *Proc. Natl Acad. Sci.* 90: 10613–10617 (1993), and Kaplitt et al., *Nature Genet.* 8:148–153 (1994).

In another embodiment of the invention, a metastatic marker gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for metastatic marker polynucleotides. Alpha viruses are described in WO 94/21792, WO 92/10578 and WO 95/07994. Several different alphavirus gene delivery vehicle systems can be constructed and used to deliver metastatic marker subgenomic polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent subgenomic fragment transcription, and a Sindbis RNA polymerase recognition sequence. Optionally, the viral junction region can be modified so that subgenomic polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the subgenomic polynucleotide and a second viral junction region which has been modified such that subgenomic polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450.

Other viral gene delivery vehicles suitable for use in the present invention include, for example, those derived from poliovirus (Evans et al., *Nature* 339:385, 1989, and Sabin et al., *J. Biol. Standardization* 1:115, 1973) (ATCC VR-58);

rhinovirus (Arnold et al., *J. Cell. Biochem.* L401, 1990) (ATCC VR-1110); pox viruses, such as canary pox virus or vaccinia virus (Fisher-Hoch et al., *PNAS* 86:317, 1989; Flexner et al., *Ann. N.Y Acad. Sci.* 569:86, 1989; Flexner et al., *Vaccine* 8:17, 1990; U.S. Pat. Nos. 4,603,112 and 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); influenza virus (Luytjes et al., *Cell* 59:1107, 1989; McMicheal et al., *The New England Journal of Medicine* 309:13, 1983; and Yap et al., *Nature* 273:238, 1978) (ATCC VR-797); parvovirus such as adeno-associated virus (Samulski et al., *J. Vir.* 63:3822, 1989, and Mendelson et al., *Virology* 166:154, 1988) (ATCC VR-645); herpes simplex virus (Kit et al., *Adv. Exp. Med. Biol.* 215:219, 1989) (ATCC VR-977; ATCC VR-260); Nature 277:108, 1979); human immunodeficiency virus (EPO 386,882, Buchschacher et al., *J. Vir.* 66:2731, 1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241). Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740).

A subgenomic metastatic marker polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994).

In an alternative embodiment, a metastatic marker subgenomic polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell., however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, *Biochemistry, pp.* 236–240, 1975 (W. H. Freeman, San Francisco, Calif.); Szoka et al., *Biochim. Biophys. Acta* 600:1, 1980; Bayer et al., *Biochim. Biophys. Acta.* 550:464, 1979; Rivnay et al., *Meth. Enzymol.* 149:119, 1987; Wang et al., *PNAS* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising metastatic marker subgenomic polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Nat'l Acad. Sci. USA* 84:7413–7416, 1987), mRNA (Malone et al., *Proc. Nat'l Acad. Sci. USA* 86:6077–6081, 1989),. and purified transcription factors (Debs et al., *J. Biol. Chem.* 265:10189–10192, 1990), in functional form. Cationic liposomes are readily available. For example, N[1,2,3-dioleyloxy)propyl]-N,N,N-triethylammonium (DOTMA) liposomes are available under the trademark Lipofectin, from GIBCO BRL, Grand Island, N.Y. See also Felgner et al., *Proc. Nat'l Acad. Sci USA* 91: 5148–5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., *Proc. Nat'l Acad. Sci. USA* 75:4194–4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., *Methods of Immunology (1983)*, Vol. 101, pp. 512–527; Szoka et al., *Proc. Nat'l Acad Sci. USA* 87:3410–3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun.* 76:836, 1977; Fraley et al., *Proc. Nat'l Acad. Sci. USA* 76:3348, 1979; Enoch and Strittmatter, *Proc. Nat'l Acad Sci. USA* 76:145, 1979; Fraley et a., *J. Biol. Chem.* 255:10431, 1980; Szoka and Papahadjopoulos, *Proc. Nat'l Acad. Sci USA* 75:145, 1979; and Schaefer-Ridder et al., *Science* 215:166, 1982.

In addition, lipoproteins can be included with a metastatic marker subgenomic polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked metastatic marker subgenomic polynucleotide molecules are used as gene delivery vehicles, as described in WO 90/11092 and U.S. Pat. No. 5,580,859. Such gene delivery vehicles can be either metastatic marker DNA or RNA and, in certain embodiments, are linked to killed adenovirus. Curiel et al., *Hum. Gene. Ther.* 3:147–154, 1992. Other suitable vehicles include DNA-ligand (Wu et al., *J. Biol. Chem.* 264:16985–16987, 1989), lipid-DNA combinations (Felgner et al., *Proc. Nat'l Acad. Sci. USA* 84:7413 7417, 1989), liposomes (Wang et al., *Proc. Nat'l Acad. Sci.* 84:7851–7855, 1987) and microprojectiles (Williams et al., *Proc. Nat'l Acad Sci* 88:2726–2730, 1991).

One can increase the efficiency of naked metastatic marker subgenomic polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. Metastatic marker subgenomic polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of metastatic marker subgenomic polynucleotides into the cytoplasm.

The invention provides a method of detecting metastatic marker gene expression in a biological sample. Detection of metastatic marker gene expression is useful, for example, for identifying metastases or for determining metastatic potential in a tissue sample, preferably a tumor. Appropriate treatment regimens can then be designed for patients who are at risk for developing metastatic cancers in other organs of the body.

The body sample can be, for example, a solid tissue or a fluid sample. Protein or nucleic acid expression products can be detected in the body sample. In one embodiment, the body sample is assayed for the presence of a metastatic marker protein. A metastatic marker protein comprises a sequence encoded by a nucleotide sequence shown in SEQ ID NOS:1–85 or its complement and can be detected using the marker protein-specific antibodies of the present invention. The antibodies can be labeled, for example, with a radioactive, fluorescent, biotinylated, or enzymatic tag and detected directly, or can be detected using indirect immunochemical methods, using a labeled secondary antibody. The presence of the metastatic marker proteins can be assayed, for example, in tissue sections by immunocytochemistry, or in lysates, using Western blotting, as is known in the art.

In another embodiment, the body sample is assayed for the presence of marker protein mRNA. A sample can be contacted with a nucleic acid hybridization probe capable of hybridizing with the mRNA corresponding the selected polypeptide. Still further, the sample can be subjected to a Northern blotting technique to detect mRNA, indicating expression of the polypeptide. For those techniques in which mRNA is detected, the sample can be subjected to a nucleic acid amplification process whereby the mRNA molecule or a selected part thereof is amplified using appropriate nucleotide primers. Other RNA detection techniques can also be used, including, but not limited to, in situ hybridization.

Marker protein-specific probes can be generated using the cDNA sequences disclosed in SEQ ID NOS:1–85. The probes are preferably at least 15 to 50 nucleotides in length, although they can be at least 8, 10, 11, 12, 20, 25, 30, 35, 40, 45, 60, 75, or 100 or more nucleotides in length. The probes can be synthesized chemically or can be generated from longer polynucleotides using restriction enzymes. The probes can be labeled, for example, with a radioactive, biotinylated, or fluorescent tag.

Optionally, the level of a particular metastatic marker expression product in a body sample can be quantitated. Quantitation can be accomplished, for example, by comparing the level of expression product detected in the body sample with the amounts of product present in a standard curve. A comparison can be made visually or using a technique such as densitometry, with or without computerized assistance. For use as controls, body samples can be isolated from other humans, other non-cancerous organs of the patient being tested, or non-metastatic breast or colon cancer from the patient being tested.

Polynucleotides encoding metastatic marker-specific reagents of the invention, such as antibodies and nucleotide probes, can be supplied in a kit for detecting marker gene expression products in a biological sample. The kit can also contain buffers or labeling components, as well as instructions for using the reagents to detect the marker expression products in the biological sample.

If expression of a metastatic marker gene having a nucleotide sequence shown in SEQ ID NOS:2, 4, 9, 13, 14, 19, 26, 29, 39–41, 48, 55, 57, 60, 63, 64, 72, 73, 82, or 83 is detected, the biological sample contains cancer cells which will likely metastasize to the lung. If expression of a metastatic marker gene having a nucleotide sequence shown in SEQ ID NOS:1, 5, 11, 18, 20, 22, 24, 30, 33, 35, 36, 38, 45, 52, 58, 65, 66, 70, 74, 76, or 80 is detected, the biological sample contains cancer cells which will likely metastasize to the bone and/or lung. On the other hand, if expression of a metastatic marker gene having a nucleotide sequence shown in SEQ ID NOS:3, 7, 8, 10, 12, 15–17, 21, 23, 25, 28, 31, 34, 37, 42–44, 46, 47, 49–51, 53, 59, 61, 62, 67, 68, 75, 77–79, 81, 84, or 85 is detected, the biological sample contains cancer cells which will likely not metastasize. Detection of expression of a metastatic marker gene comprising the nucleotide sequence shown in SEQ ID NO:56 also indicates that the biological sample contains cancer cells which will likely metastasize. This information can be used, for example, to design treatment regimens. Treatment regiments can include altering expression of one or more metastatic marker genes, as desired. Metastatic marker gene expression can be altered for therapeutic purposes, as described below, or can be used to identify therapeutic agents.

In one embodiment of the invention, expression of a metastatic marker gene whose expression is up-regulated in metastatic cancer is decreased using a ribozyme, an RNA molecule with catalytic activity. See, e.g., Cech, 1987, *Science* 236: 1532–1539; Cech, 1990, *Ann. Rev. Biochem.* 59:543–568; Cech, 1992, *Curr. Opin. Struct. Biol.* 2: 605–609; Couture and Stinchcomb, 1996, *Trends Genet.* 12: 510–515. Ribozymes can be used to inhibit gene function by cleaving an RNA sequence, as is known in the art (e.g., Haseloff et al., U.S. Pat. No. 5,641,673).

Coding sequences of metastatic marker genes can be used to generate ribozymes which will specifically bind to mRNA transcribed from a metastatic marker gene. Methods of designing and constructing ribozymes which can cleave other RNA molecules in trans in a highly sequence specific manner have been developed and described in the art (see Haseloff, J. et al. (1988), *Nature* 334:585–591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach, W. L. et al., *EP* 321,201). Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

Ribozymes can be introduced into cells as part of a DNA construct, as is known in the art. The DNA construct can also include transcriptional regulatory elements, such as a promoter element, an enhancer or UAS element, and a transcriptional terminator signal, for controlling the transcription of the ribozyme in the cells.

Mechanical methods, such as microinjection, liposome-mediated transfection, electroporation, or calcium phosphate precipitation, can be used to introduce a ribozyme-containing DNA construct into cells whose division it is desired to decrease, as described above. Alternatively, if it is desired that a DNA construct be stably retained by the cells, the DNA construct can be supplied on a plasmid and maintained as a separate element or integrated into the genome of the cells, as is known in the art.

As taught in Haseloff et al., U.S. Pat. No. 5,641,673, ribozymes can be engineered so that their expression will occur in response to factors which induce expression of metastatic marker genes. Ribozymes can also be engineered to provide an additional level of regulation, so that destruction of mRNA occurs only when both a ribozyme and a metastatic marker gene are expressed in the cells.

Expression of a metastatic marker gene can also be altered using an antisense oligonucleotide sequence. The antisense sequence is complementary to at least a portion of the coding sequence of a metastatic marker gene having a nucleotide sequence shown in SEQ ID NOS:1–85. The complement of a nucleotide sequence shown in SEQ ID NOS:1–85 is a contiguous sequence of nucleotides which form Watson-Crick basepairs with a contiguous nucleotide sequence shown in SEQ ID NOS: 1–85.

Preferably, the antisense oligonucleotide sequence is at least six nucleotides in length, but can be at least about 8, 12, 15, 20, 25, 30, 35, 40, 45, or 50 nucleotides long. Longer sequences can also be used. Antisense oligonucleotide molecules can be provided in a DNA construct and introduced into cells whose division is to be decreased, as described above.

Antisense oligonucleotides can comprise deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1–8; Sonveaux, 1994, *Meth. Mol. Biol.* 26:1–72; Uhlmann et al., 1990, *Chem. Rev.* 90:543–583.

Although precise complementarity is not required for successful duplex formation between an antisense molecule and the complementary coding sequence of a metastatic marker gene, antisense molecules with no more than one mismatch are preferred. One skilled in the art can easily use the calculated melting point of a metastatic marker gene antisense-sense pair to determine the degree of mismatching which will be tolerated between a particular antisense oligonucleotide and a particular coding sequence of the selected gene.

Antisense oligonucleotides can be modified without affecting their ability to hybridize to a metastatic marker protein coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. Agrawal et al., 1992, Trends Biotechnol. 10:152–158; Uhlmann et al., 1990, *Chem. Rev.* 90:543–584; Uhlmann et al., 1987, *Tetrahedron. Lett.* 215:3539–3542.

Antibodies of the invention which specifically bind to a metastatic marker protein can also be used to alter metastatic marker gene expression. By antibodies is meant antibodies and parts or derivatives thereof, such as single chain antibodies, that retain specific binding for the protein. Specific antibodies bind to metastatic marker proteins and prevent the proteins from functioning in the cell. Polynucleotides encoding specific antibodies of the invention can be introduced into cells, as described above.

Marker proteins of the present invention can be used to screen for drugs which have a therapeutic anti-metastatic effect. The effect of a test compound on metastatic marker protein synthesis can also be used to identify test compounds which modulate metastasis. Test compounds which can be screened include any substances, whether natural products or synthetic, which can be administered to the subject. Libraries or mixtures of compounds can be tested. The compounds or substances can be those for which a pharmaceutical effect is previously known or unknown.

A cell is contacted with a test compound. The cell can be any cell, such as a colon cancer cell, which ordinarily synthesizes the metastatic marker protein being measured. For example, Tables 1 and 2 provide appropriate cell types which can be used for screening assays.

Synthesis of metastatic marker proteins can be measured by any means for measuring protein synthesis known in the art, such as incorporation of labeled amino acids into proteins and detection of labeled metastatic marker proteins in a polyacrylamide gel. The amount of metastatic marker proteins can be detected, for example, using metastatic marker protein-specific antibodies of the invention in Western blots. The amount of the metastatic marker proteins synthesized in the presence or absence of a test compound can be determined by any means known in the art, such as comparison of the amount of metastatic marker protein synthesized with the amount of the metastatic marker proteins present in a standard curve.

The effect of a test compound on metastatic marker protein synthesis can also be measured by Northern blot analysis, by measuring the amount of metastatic marker protein mRNA expression in response to the test compound using metastatic marker protein specific nucleotide probes of the invention, as is known in the art.

Typically, biological sample is contacted with a range of concentrations of the test compound, such as 1.0 nM, 5.0 nM, 10 nM, 50 nM, 100 nM, 500 nM, 1 mM, 10 mM, 50 mM, and 100 mM. Preferably, the test compound increases or decreases expression of a metastatic marker protein by 60%, 75%, or 80%. More preferably, an increase or decrease of 85%, 90%, 95%, or 98% is achieved.

The invention provides compositions for increasing or decreasing expression of metastatic marker protein. Therapeutic compositions for increasing metastatic marker gene expression are desirable for markers which are down-regulated in metastatic cells. These compositions comprise polynucleotides encoding all or at least a portion of a metastatic marker protein gene expression product. Preferably, the therapeutic composition contains an expression construct comprising a promoter and a polynucleotide segment encoding at least a portion of the metastatic marker protein which is effective to increase or decrease metastatic potential. Portions of metastatic marker genes or proteins which are effective to decrease metastatic potential of a cell can be determined, for example, by introducing various portions of metastatic marker genes or polypeptides into metastatic cell lines, such as MDA-MB-23 1, MDA-MB-435, Km12C, or Km12L4, and assaying the division rate of the cells or the ability of the cells to form metastases when implanted in vivo, as is known in the art. Non-metastatic cell lines, such as MCF-7, can be used to assay the ability of a portion of a metastatic marker protein to increase expression of a metastatic marker gene.

Within the expression construct, the polynucleotide segment is located downstream from the promoter, and transcription of the polynucleotide segment initiates at the promoter. A more complete description of gene transfer vectors, especially retroviral vectors is contained in U.S. Ser. No. 08/869,309, which is incorporated herein by reference.

Decreased metastatic marker gene expression is desired in conditions in which the marker gene is up-regulated in metastatic cancer. Therapeutic compositions for treating these disorders comprise a polynucleotide encoding a reagent which specifically binds to a metastatic marker protein expression product, as disclosed herein.

Metastatic marker therapeutic compositions of the invention can comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates.

Therapeutic compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for the therapeutic composition.

Typically, a therapeutic metastatic marker composition is prepared as an injectable, either as a liquid solution or suspension; however, solid forms suitable for solution in, or suspension in, liquid vehicles prior to injection can also be prepared. A metastatic marker composition can also be formulated into an enteric coated tablet or gel capsule according to known methods in the art, such as those described in U.S. Pat. No. 4,853,230, EP 225,189, AU 9,224,296, and AU 9,230,801.

Administration of the metastatic marker therapeutic agents of the invention can include local or systemic administration, including injection, oral administration, particle gun, or catheterized administration, and topical administration. Various methods can be used to administer a therapeutic metastatic marker composition directly to a specific site in the body.

For treatment of tumors, including metastatic lesions, for example, a therapeutic metastatic marker composition can be injected several times in several different locations within the body of tumor. Alternatively, arteries which serve a tumor can be identified, and a therapeutic composition injected into such an artery, in order to deliver the composition directly into the tumor.

A tumor which has a necrotic center can be aspirated and the composition injected directly into the now empty center of the tumor. A therapeutic metastatic marker composition can be directly administered to the surface of a tumor, for example, by topical application of the composition. X-ray imaging can be used to assist in certain of the above delivery methods. Combination therapeutic agents, including a metastatic marker proteins or polypeptide or a metastatic marker subgenomic polynucleotide and other therapeutic agents, can be administered simultaneously or sequentially.

Receptor-mediated targeted delivery can be used to deliver therapeutic compositions containing metastatic marker subgenomic polynucleotides, proteins, or reagents such as antibodies, ribozymes, or antisense oligonucleotides to specific tissues. Receptor-mediated delivery techniques are described in, for example, Findeis et al. (1993), *Trends in Biotechnol.* 11, 202–05; Chiou et al. (1994), Gene Therapeutics: Methods and Applications of Direct Gene Transfer (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Nat'l Acad. Sci. U.S.A.* 87, 3655–59; Wu et al. (1991), *J. Biol. Chem.* 266, 338–42.

Alternatively, a metastatic marker therapeutic composition can be introduced into human cells ex vivo, and the cells then replaced into the human. Cells can be removed from a variety of locations including, for example, from a selected tumor or from an affected organ. In addition, a therapeutic composition can be inserted into non-affected, for example, dermal fibroblasts or peripheral blood leukocytes. If desired, particular fractions of cells such as a T cell subset or stem cells can also be specifically removed from the blood (see, for example, PCT WO 91/16116). The removed cells can then be contacted with a metastatic marker therapeutic composition utilizing any of the above-described techniques, followed by the return of the cells to the human, preferably to or within the vicinity of a tumor or other site to be treated. The methods described above can additionally comprise the steps of depleting fibroblasts or other non-contaminating tumor cells subsequent to removing tumor cells from a human, and/or the step of inactivating the cells, for example, by irradiation.

Both the dose of a metastatic marker composition and the means of administration can be determined based on the specific qualities of the therapeutic composition, the condition, age, and weight of the patient, the progression of the disease, and other relevant factors. Preferably, a therapeutic composition of the invention increases or decreases expression of the metastatic marker genes by 50%, 60%, 70%, or 80%. Most preferably, expression of the metastatic marker genes is increased or decreased by 90%, 95%, 99%, or 100%. The effectiveness of the mechanism chosen to alter expression of the metastatic marker genes can be assessed using methods well known in the art, such as hybridization of nucleotide probes to mRNA of the metastatic marker genes, quantitative RT-PCR, or detection of an the metastatic marker proteins using specific antibodies of the invention.

If the composition contains the metastatic marker proteins, polypeptide, or antibody, effective dosages of the composition are in the range of about 5 $\mu$g to about 50 $\mu$g/kg of patient body weight, about 50 µg to about 5 mg/kg, about 100 µg to about 500 µg/kg of patient body weight, and about 200 to about 250 µg/kg.

Therapeutic compositions containing metastatic marker subgenomic polynucleotides can be administered in a range of about 100 ng to about 200 mg of DNA for local administration. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action and efficacy of transformation and expression are considerations that will affect the dosage required for ultimate efficacy of the metastatic marker subgenomic polynucleotides. Where greater expression is desired over a larger area of tissue, larger amounts of metastatic marker subgenomic polynucleotides or the same amounts readministered in a successive protocol of administrations, or several administrations to different adjacent or close tissue portions of, for example, a tumor site, can be required to effect a positive therapeutic outcome. In all cases, routine experimentation in clinical trials will determine specific ranges for optimal therapeutic effect.

Expression of an endogenous metastatic marker gene in a cell can also be altered by introducing in frame with the endogenous metastatic marker gene a DNA construct comprising a metastatic marker protein targeting sequence, a regulatory sequence, an exon, and an unpaired splice donor site by homologous recombination, such that a homologously recombinant cell comprising the DNA construct is formed. The new transcription unit can be used to turn the metastatic marker gene on or off as desired. This method of affecting endogenous gene expression is taught in U.S. Pat. No. 5,641,670, which is incorporated herein by reference.

The targeting sequence is a segment of at least 10, 12, 15, 20, or 50 contiguous nucleotides selected from the nucleotide sequences shown in SEQ ID NOS:1–85 or the complements thereof. The transcription unit is located upstream of a coding sequence of the endogenous metastatic marker protein gene. The exogenous regulatory sequence directs transcription of the coding sequence of the metastatic marker genes.

A metastatic marker subgenomic polynucleotide can also be delivered to subjects for the purpose of screening test compounds for those which are useful for enhancing transfer of metastatic marker subgenomic polynucleotides to the cell or for enhancing subsequent biological effects of metastatic marker subgenomic polynucleotides within the cell. Such biological effects include hybridization to complementary metastatic marker mRNA and inhibition of its translation, expression of a metastatic marker subgenomic polynucleotide to form metastatic marker mRNA and/or metastatic marker protein, and replication and integration of a metastatic marker subgenomic polynucleotide. The subject can be a cell culture or an animal, preferably a mammal, more preferably a human.

Test compounds which can be screened include any substances, whether natural products or synthetic, which can be administered to the subject. Libraries or mixtures of compounds can be tested. The compounds or substances can be those for which a pharmaceutical effect is previously known or unknown. The compounds or substances can be delivered before, after, or concomitantly with a metastatic marker subgenomic polynucleotide. They can be administered separately or in admixture with a metastatic marker subgenomic polynucleotide.

Integration of a delivered metastatic marker subgenomic polynucleotide can be monitored by any means known in the art. For example, Southern blotting of the delivered metastatic marker subgenomic polynucleotide can be performed. A change in the size of the fragments of a delivered polynucleotide indicates integration. Replication of a delivered polynucleotide can be monitored inter alia by detecting incorporation of labeled nucleotides combined with hybridization to a metastatic marker probe. Expression of metastatic marker subgenomic polynucleotide can be monitored by detecting production of metastatic marker mRNA which hybridizes to the delivered polynucleotide or by detecting metastatic marker protein. Metastatic marker protein can be detected immunologically. Thus, the delivery of metastatic marker subgenomic polynucleotides according to the present invention provides an excellent system for screening test compounds for their ability to enhance transfer of metastatic marker subgenomic polynucleotides to a cell, by enhancing delivery, integration, hybridization, expression, replication or integration in a cell in vitro or in an animal, preferably a mammal, more preferably a human.

The above disclosure generally describes the present invention. A more complete understanding can be obtained by reference to the following specific examples which are provided herein for purposes of illustration only, and are not intended to limit the scope of the invention.

EXAMPLE 1

Differentially Expressed Genes

This example demonstrates polynucleotides that are differentially expressed in human breast or colon cancer cell lines.

Human cell lines used to identify differentially expressed polynucleotides are the human breast cancer cell lines MCF-7 (non-metastatic), MDA-MB-231 (metastatic to bone and/or lung), and MDA-MB-435 (metastatic to lung) (Brinkley and Cailleau, 1980, *Cancer Res.* 40:3118), and the colon cancer cell lines Km12C (low metastatic) and Km124A (highly metastatic) (Morikawa et al., 1988, *Cancer Res.* 48:1943–1948).

RNA was prepared from each cell line and reverse transcribed to form cDNA. The cDNA was amplified using random primers. Amplification products were visualized on a sequencing gel, and cDNA corresponding to mRNA which was differentially expressed in the cell lines was identified.

Expression patterns and sequence identification numbers of novel metastatic marker polynucleotides are shown in Table 1.

Expression patterns and sequence identification numbers of metastatic marker polynucleotides which correspond to known genes are shown in Table 2, and the corresponding proteins are described below.

Osteopontin (SEQ ID NO:64) (OPN or Sppl for secreted phosphoprotein 1) is a secreted extracellular matrix protein, often expressed during wound healing, involved in osteoclastic differentiation and activation, as described in Heymann et al., 1998, *Cytokine* 10:155–168. Osteopontin is found in bone and other epithelial cells, and has been shown to stimulate proliferation of a quiescent subpopulation of prostate epithelial cells (see Elgavish et al., 1998, *Prostate* 35:83–94).

Osteopontin is implicated during the development of diabetic nephropathy (Fischer et al., 1998, *Diabetes* 47:1512–1518); the process of cartilage-to-bone transition during rigid bone healing after bone fracture (Nakase et al., 1998, *Acta Histochem* 100:287–295); wound healing by an interaction with the receptor integrin alpha(v)beta 3 after focal stroke (Ellison et al., 1998, *Stroke* 29:1698–1706); integrin receptor binding and signaling during cell attachment and mechanical stimulation of osteoblasts (Carvalho et al., 1998, *J. Cell Biochem* 70:376–390); kidney morphogenesis (Denda et al., 1998, *Mol. Biol. Cell* 9:1425–1435); and as an interstitial chemoattractant in renal inflammation (Rovin and Phan, 1998, *Am. J. Kidney Dis.* 31:1065–1084). Mice lacking the osteopontin gene showed modulation in osteoclast differentiation from wild type mice (see Rittling et al., 1998, *J. Bone Miner Res.* 13:1101–1111).

Osteopontin is synthesized by monocytes and macrophages within injury sites, and can promote leukocyte adhesion through the alpha 4beta1 integrin, as described in Bayless et al., 1998, *J. Cell Sci.* 111:1165–1174. Osteopontin is transcriptionally regulated by retinoic acid (see Manji et al., 1998, *J. Cell Physiol.* 176:1–9); preferentially expressed in high grade metastatic brain tumors compared to low grade brain tumors, and inducible by tissue plasminogen activator (tPA) in glioma cell lines (see Tucker et al., 1998, *Anticancer Res.* 18:807–812). Osteopontin is expressed in about 73% of primary gastric carcinoma tissues and correlated with the progression of human gastric carcinoma and lymphogenous metastasis (see Ue et al., 1998, *Int. J. Cancer* 79:127–132).

Nip (SEQ ID NO:65) is described in Boyd et al., 1994, *Cell* 79:341–351. Adenovirus E1B 19 kDa protein protects against cell death induced by viral infection and external stimuli, and can be functionally substituted with the Bcl-2 protoncogene. E1B 19 kDa interacting proteins (Nip1, Nip2, and Nip3) were discovered in yeast two-hybrid studies conducted to discern proteins that interact with 19 kDa protein, as described by Boyd et al., supra. Nip 1, 2, and 3 interact with discrete domains of E1B 19 kDa, and similarly also interact with Bcl-2, in both cases promoting cell survival.

Ca-dependent protease (SEQ ID NO:66) is $Ca^{+2}$-dependent protease (also called calpain), activity of which is present in every vertebrate cell that has been examined. $Ca^{+2}$-dependent protease activity is associated with cleavages that alter regulation of various enzyme activities, with remodeling or disassembly of the cell cytoskeleton, and with cleavages of hormone receptors (see Goll et al., 1992, *Bioessays* 14(8):549–556). $Ca^{+2}$-dependent protease activity is regulated by binding of $Ca^{+2}$ to specific sites on the calpain molecule, with binding to each site generating a specific response corelated with a specific activity (e.g., proteolytic activity, calpastatin binding, etc.), as described in Goll et al. Excessive activation of the $Ca^{+2}$-dependent protease calpain may play a role in the pathology of disorders including cerebral ischemia, cataract, myocardial ischemia, muscular dystrophy, and platelet aggregation. Therapeutic applications include selective $Ca^{+2}$-dependent protease inhibition, as described in Wang and Yuen, 1994, *Trends Pharmacol. Sci.* 15(11):412–419.

IGF-R (insulin-like growth factor receptor) (SEQ ID NO:67) is a transmembrane tyrosine kinase linked to the ras-raf-MAPK(mitogen-activated protein kinase) cascade and required for the cell to progress through the cell cycle (Werner and Roith, 1997, *Crit. Rev. Oncog* 8(1):71–92). IGF-R mediates mitogenesis, growth hormone action, cell survival and transformation and in maintenance of the malignant phenotype. IGF-R is a member of the growth factor receptor tyrosine kinase superfamily, exists as covalent cross-linked dimers where each monomer is composed of two subunits, and is bound by ligand in the extracellular domain (McInnes and Sykes, 1997, *Biopolymers* 43(5): 339–366).

The domains of the IGF-R are described in Sepp-Lorenzino, 1998, *Breast Cancer Res Treat* 47(3):235–253, including domains responsible for mitogenesis, transformation, and protection from apoptosis. IGF-R expression is increased in breast cancer cells derived from tumor tissue and cell lines, as described in Surmacz et al., 1998, *Breast Cancer Res Treat* 47(3):255–267, and increased IGF-R may increase tumor mass and/or aid tumor recurrence by promoting proliferation, cell survival, and cell-cell interactions. Human pancreatic cancers overexpress IGF-R and its ligand (Korc, 1998, *Surg Oncol Clin N Am* 7(1): 25–41), and expression of IGF-I and IGF-R is determined to be a prognostic factor (reflecting the interaction between the neoplastic cells and their microenvironment) for lymphocytic infiltration in thryoid carcinomas (Fonseca et al., 1997, *Verh Dtsch Ges Pathol* 81:82–96).

ILGF-BP5 (SEQ ID NO:68) is insulin-like growth factor binding protein 5, described in Allander et al., 1994, *J. Biol. Chem.* 269:10891–10898. The gene and promoter for IGF-BP5 are characterized by Allander et al., 1994, *J. Biol Chem.* 269:10891–10898, and some general actions of IGF-BPs are described in Chan and Spencer, 1997, *Endocrine* 7:95–97. Potential impact of IGF-BPs on cancer cell growth is described in Oh, 1997, *Endocrine* 7:111–113, and Oh, 1998, *Breast Cancer Res Treat* 47:283–293. IGF-BP5 is expressed during brain development: IGF-BP5 and IGF-1 mRNAs are synchronously coexpressed in principal neurons of sensory relay systems, including the olfactory bulb, medial and dorsal lateral geniculate bodies, and ventral tier, cochlear, lemniscal, and vestibular nuclei, and are transiently coexpressed in principal neurons of the anterodorsal nucleus, as described in Bondy and Lee, 1993, *J. Neurosci* 13(12): 5092–5104. IGF-BP5 is expressed by luminal or cumulus granulosa cells in virtually all follicles, and is highly abundant in stromal interstitial cells of the mature ovary (see Zhou and Bondy, 1993, *Biol. Reprod* 48:467–482). IGF-BP5 induction is strongly stimulated during differentiation of skeletal myoblasts and is correlated with IGF-R activation as described in Rousse et al., 1998, *Endocrinology* 139:1487–1493. IGF-BP5 and other components of the IGF system are critical in postnatal brain development (see Lee et al., 1996, *J. Cereb Blood Flow Metab* 16:227–236).

IGF-BP5 stimulates bone cell proliferation by an IGF-independent mechanism involving IGF-BP5-specific cell surface binding sites, as described in Mohan et al., 1995, *J. Biol Chem* 270:20424–20431. In connective tissue cell types, IGF-BP5 has a lowered binding affinity to the extracellular matrix which allows IGF-I to better equilibrate with the receptors which in turn potentiates IGF-I action on fibroblasts and smooth muscle cells (Clemmons, *Mol Cell Endocrinology* 140:19–24).

Lactate dehydrogenase (SEQ ID NO:69) is a member of the LDH group of tetrameric enzymes with five isoforms composed of combinations of two subunits, LDH-A and LDH-B. Shim et al., 1997, *Proc. Nat'l Acad. Sci.* 94:6658–6663, described the relationship between LDH-A and neoplasia. In particular, overexpression on LDH-A may contribute to altered metabolism that confers neoplastic growth advantage. The expression pattern of LDH in the present invention is consistent, in that LDH expression is higher in two metastatic breast cancer cell lines than in a non-metastatic breast cancer cell line (Table 2). High or increasing lactate dehydrogenase (LDH) levels in tumor tissue and cells is associated with poor survival rate in small cell lung carcinoma (SCLC), as described in Ray et al., 1998, *Cancer Detect Prev* 22:293–304, making it a useful prognostic indicator for SCLC as discussed in Stokkel et al., 1998, *J. Cancer Res Clin Oncol* 124:215–219.

Ufo TKR (SEQ ID NO:70) is described in Schulz et al., 1993, *Oncogene* 8:509–513. This protein has been reported as a marker in tumors, but has not previously been reported in breast cancer. According to the present invention, expression is found in the MDA-MB-231 breast cancer cell line, but not in the MSF-7 or MDA-MB-435 cell lines. This gene and protein provide new markers for distinguishing breast cancer tissue of different types of metastatic potential.

Initially isolated from primary human myeloid leukemia cells, the ufo oncogene (also called Axl or Ark) is a receptor tyrosine kinase (RTK). Its genomic structure is described in Schulz et al., supra., and its differential expression is described in Challier et al., 1996, *Leukemia* 10:781–787. The ufo protein is a member of a class of RTKs having two fibronectin type III domains and two immunoglobulin-like domains present in the extracellular portion, and is preferentially expressed in monocytes, stromal cells, and some CD34-positive progenitor cells (Neubauer et al., 1997, *Leuk Lymphoma* 25:91–96). Ufo has an extracellular structure similar to neural cell adhesion molecules. and has direct or indirect binding sites for PLCgamma, GRB2, c-src, and lck (Braunger et al., 1997, *Oncogene* 14:2619–2631).

eIF-2 (SEQ ID NO:71) is a translation initiation factor, and functions as a heterotrimeric GTP-binding protein involved in the recruitment of methionyl-tRNA to the 40 S ribosomal subunit (Gasper et al., 1994, *J. Biol. Chem.* 269:3415–3422). According to the present invention, higher expression is found in two metastatic breast cancer cell lines and not in cell line MCF-7.

eIF-2 is involved in introducing the initiator tRNA into the translation mechanism and performing the first step in the peptide chain elongation cycle. eIF-2 is associated with a 5 subunit molecule having GTP recycling function called eIF-2B (Kyrpides and Woese, 1998, *Proc. Nat'l Acad. Sci. USA* 95:3726–3730, and Kimball et al., 1998, *J. Biol. Chem.* 273:12841–12845).

eIF-2 has subunits alpha and beta. eIF-2alpha is phosphorylated at Ser 51 and then modulates the interaction of eIF-2 and eIF-2B, as described in Kimball et al., 1998, *Protein Expr. Purif.* 12:415–419, Kimball et al., 1998, *J. Biol. Chem.* 273:3039–3044, and Pavitt 1998, *Genes Dev.* 12:514–526. It is reported that by regulating translation initiation, control of cell growth and division in eukaryotic cells is achieved: for example, clotrimazole, a potent antiproliferative agent in vitro and in vivo, depletes intracellular $Ca^{+2}$ stores, which activates PKR, resulting in the phosphorylation of eIF-2alpha, and the ultimate inhibition of protein synthesis and blockage of the cell cycle in GI phase (Aktas et al., 1998, *Proc. Nat'l Acad. Sci. USA* 95:8280–8285). Additionally, Kim et al., 1998, *Mol. Med.* 4:179–190, show that nitric oxide (NO) suppresses protein synthesis in cell types including human ovarian tumor cells by stimulating phosphorylation of eIF-2alpha.

Glutaminyl cyclase (SEQ ID NO:72) is described by Song et al., 1994, *J. Mol. Endocrinol.* 13:77–86, and is expressed most highly in the most metastatic cell line MDA-MB435, as compared to less metastatic line MDA-MB-231 and non-metastatic line MCF-7. Glutaminyl cyclase (also called glutamine cyclotransferase) converts glutaminyl-peptides (such as gonadotropin-releasing hormone and thyrotropin-releasing hormone) into pyroglutamyl-peptides, as described in Busby et al., 1987, *J. Biol. Chem.* 262:8532–8536, Fischer and Spiess, 1987. *Proc. Nat'l Acad. Sci. USA* 84:3628–3632, and Pohl et al., 1991, *Proc. Nat'l Acad. Sci.* 88:10059–10063. Cloning and sequence analysis of glutaminyl cyclase derived from a human pituitary cDNA library is described in Song et al., 1994. J. Mol. Endocrinol. 13:77–86. Studies on the catalytic pathway of glutaminyl cyclase and its substrate specificity are described in Gololobov et al., 1996, *Biol. Chem. Hoppe Seyler* 377:395–398. Assays for the presence of glutaminyl cyclase activity are described in Koger et al., 1989, *Method Enzymol.* 168:358–365 and Houseknecht et al., 1998, *Biotechniques* 24:346.

gp130 (SEQ ID NO:73) is transmembrane protein glycoprotein 130. gp130 is a signal transducing shared component of the receptor complexes for the interleukin-6 (IL-6)-type cytokines (Hirano et al., 1997, *Cytokine Growth Factor Rev.* 8:241–252), including IL-6, IL-11, leukemia inhibitor factor (LIF), oncostatin M (OSM), ciliary neurotrophic factor and cardiotrophin-1. The N-terminal of gp130 is an extracellular immunoglobulin-like portion of the protein (Hammacher et al., 1998, *J. Biol. Chem.* 273:22701–22707). Signal transduction including gp130 occurs through the gp130/Jak/STAT pathway 1 (Heinrich 1998, *Biochem. J.* 334:297–314). The cytokines acting through the pathway that includes gp130 (also called gp130 cytokines) exhibit pleitropic biological activities including immune, hematopoietic, and neural effects (Nakashima and Taga, 1998, *Semin Hematol.* 35:210–221, Thompson et al., 1998, *Neuroscience* 84:1247–1255, Hirano, 1998, Int. Rev. Immunol. 16:249–284, Marz et al., 1997, *Eur. J. Neurosci.* 9:2765–2773, and Betz and Muller, 1998, *Int Immunol* 10:1175–1184).

gp130 cytokines are reported to control survival and proliferation of myeloma cell lines and primary myeloma cells (Klein, 1998, *Curr. Opin. Hematol.* 5:186–191). gp130 is expressed in the majority of renal cell carcinomas and has an important role in the proliferation of some renal cell carcinoma cell lines (Costes et al., 1997, *J. Clin. Pathol.* 50:835–840).

E-cadherin (SEQ ID NO:75) is a member of a family of glycoproteins responsible for calcium-dependent cell-cell adhesion and is implicated in maintaining cytoskeletal integrity. Epithelial cadherin (E-cadherin) mediated cell adhesion system in cancer cells is inactivated by multiple mechanisms corresponding to the pathological features of the particular tumor type (Hirohashi, 1998, *Am J. Pathol* 153:333–339). In general the cadherin system mediates $Ca^{+2}$-dependent homophilic cell-cell adhesion. Transcriptional inactivation of E-cadherin expression occurs frequently in tumor progression, and thus inactivation or downregulation of E-cadherin plays a significant role in mulistage carcinogenesis (Hirohashi, 1998, *Am J Pathol* 153:333–339).

E-cadherin is characterized as a tumor suppressor of the metastatic phenotype, as described in MacGrogan and Bookstein, 1997, *Semin Cancer Biol* 8:11–19, and cadherins are important determinants of tissue morphology including invasive carcinoma as described in van der Linden, 1996, *Early Pregnancy* 2:5–14, and Yap, 1998, *Cancer Invest.* 16:252–261.

Mechanisms of action of cadherins are discussed in Daniel and Reynolds, 1997, *Bioessays* 19:883–891. The structure and function of cell adhesion molecules including E-cadherin are described in Joseph-Silverstein and Silverstein, 1998, *Cancer Invest.* 16:176–182, Yap et al., 1997, *Annu. Rev. Cell Dev. Biol.* 13:119–146, and Uemura, 1998, *Cell* 93:1095–1098. Cell adhesion molecules including E-cadherin are potential targets for anti-cancer drugs and therapeutics to treat acute or chronic inflammatory disease as described in Buckley and Simmons, 1997, *Mol Med Today* 3:449–456, Moll and Moll, 1998, *Virchows Arch* 432:487–504.

According to the present invention, E-cadherin is expressed in non-metastatic breast cancer cell line MCF-7, and not in MDA-MB-231 and MDA-MB4435. The expression products are diagnostic markers indicating the metastatic potential of breast cancer tissue samples.

Serpin (SEQ ID NO:76), serine protease inhibitors, are a family of protease inhibitors that inhibit chymotrypsin-like serine proteases (Whisstock et al., 1998, *Trends Biochem. Sci.* 23:63–67) and that have the unique ability to regulate their activity by changing the conformation of their reactive-center loop; studies of serpin variants provide definition for the functional domains of serpins that control the folding and link serpins mutations to disease (see Stein and Carrell, 1995, *Nat. Struct. Biol.* 2:96–113). Serine protease cleavage of proteins is essential to a wide variety of biological processes, and the cleavage is primarily regulated by the cleavage inhibitors, as described in Wright, 1996, *Bioessays* 18:453464. Members of the serpin family include alpha 1-antitrypsin (AAT) (Carrell et al., 1996, *Chest* 110:243S-247S), alpha2-anti-plasmin (PAI-1 and PAI-2) (Andreasen et al., 1997, *Int. J. Cancer* 72:1–22), thrombin, urokinase plasminogen activator, and kallikrein (Turgeon and Houenou, 1997, *Brain Res Brain Res Rev* 25:85–95). Some serpins also have other activities including neuronal differentiating and survival activities (Becerra, 1997, Adv. Exp. Med. Biol. 425:332–237) and tumor suppression (Sager et al., 1997, *Adv. Exp. Med. Biol.* 25:77–88). PAI-1 and PAI-2 are linked to cancer metastasis, as described in Andreasen et al., 1997, *Int. J. Cancer* 72:1–22.

pS$^2$ (SEQ ID NO:77) was isolated from MCF7 human breast cancer cells, as described in Takahashi et al., 1990, *FEBS Letters* 261:283–286. pS2 is estrogen-regulated. Speiser et al., 1997, *Anticancer Research* 17:679–684, reported that the pS2 status declined from well to poorly differentiated ovarian cancer. pS2 expression also is associated with a good prognosis in breast cancer patients. According to the present invention, pS2 is expressed in MCF-7 cells, but not in two metastatic breast cancer cell lines pS2 (presenilin-2 or trefoil factor 1 (TFF 1)) is a trefoil polypeptide normally expressed in the mucosa of the gastrointestinal tract, and found ectopically in gastrointestinal inflammatory disorders and various carcinomas (May and Westley, 1997, *J. Pathol.* 183:4–7. pS2 is expressed in breast cancers (Poulsom et al., 1997, *J. Pathol.* 183:30–38). pS2 is a pleitropic factor involved in mucin polymerization, cell motility (Modlin and Poulsom, 1997, *J. Clin. Gastroenterol* 25(1):S94–S100), cell proliferation and/or differentiation, and possibly in the nervous system (see Ribieras et al., 1998, *Biochim. Biophys. Acta.* 1378:F61-F77).

LIV-1 (SEQ ID NO:78) is an estrogen-regulated protein reported in the MCF-7 cell line (Green et al., *GeneBank submission Accession No. U41060*). According to the present invention, LIV-1 is expressed in MCF-7 cells, but not in two metastatic breast cancer cell lines.

Leucine-isoleucine-valine -1 (LIV-1) and other members of the LIV family (LIV-2, 3, and 4) are binding proteins that represent a transport system for branched chain amino acids in *E. coli* as described in Yamamoto et al., 1979, *J. Bacteriol.* 138:24–32, and Yamamoto and Anraku, 1980, *J. Bacteriol.* 144:36–44. A human homologue to LIV-1 is both estrogen and growth factor inducible in MCF-7 human breast cancer cell line (El-Tanani and Green, 1997, *J. Steroid. Biochem. Mol. Biol* 60:269–276; El-Tanani and Green, 1996, *Mol Cell Endocrinol* 124:71–77; and El-Tanani and Green, 1996, *Mol Cell Endocrinol* 121:29–35).

GTP-binding protein (SEQ ID NO:79) is a member of the family of guanine nucleotide-binding regulatory proteins, G proteins. The protein is expressed in MCF-7 cells, but not in two metastatic breast cancer cell lines.

G proteins provide signaling mechanisms for the serpentine family of receptors as described in Dhanasekaran and Prasad, 1998, *Biol. Signals Recept* 7:109–117. Studies indicate that the alpha as well as the beta gamma subunits of the GTP-binding proteins are involved in the regulation of several cellular responses, some of which responses are critical to the regulation of cell growth and differentiation (Dhanasekaran and Prasad, 1998, *Biol Signals Recept* 7:109–117). G protein coupled receptors regulate the mitogen activated protein kinase pathway as described in Russell and Hoeffler, 1996, *J. Invest. Dermatol Symp Proc* 1:119–122, and thus play a role in controlling cell growth. GTP binding proteins are also implicated in the regulation of intracellular transport as described in Ktistakis, 1998, *Bioessays* 20:495–504.

Chemokines induce various intracellular signaling pathways in natural killer cells by activating members of GTP binding proteins as described in Maghazachi and Al-Auokaty, 1998, *FASEB J.* 12:913–924. Heterotrimeric GTP binding proteins regulate distinct signaling pathways, some of which in turn regulate the activity of Na+/H+ exchanger proteins as described in Voyno-Yasenetskaya, 1998, *Biol Signals Recept* 7:118–124.

Desmoplakin (SEQ ID NO:84) is a member of a family of proteins that serve as cell surface attachment sites for cytophasmic intermediate filaments.

Vimentin (SEQ ID NO: 80) is a member of the intermediate filament gene family (Evans, 1998, *Bioessays* 20:79–86. Intermediate filaments are a major component of the cytoskeleton of higher eukaryotes. Vimentin gene knockout mice indicate degeneration of the cerebellar Purkinje cells (Galou et al., 1997, Biol Cell 89:85–97). Vimentin is positive in immunohistochemical reactions of sarcomas and related lesions (Gaudin et al., 1998, *Am J Surg Pathol* 22:148–162), and of desmoplastic small round-cell tumors and their variants (Gerald et al., 1998, *J. Clin. Oncol.* 16:3028–3036). Vimentin is also expressed in neoplasms showing follicular dendritic cell differentiation as described in Perez-Ordonez and Rosai, 1998, *Semin. Diagn. Pathol.* 15:144–154, and in biphasic carcinomatous-sarcomatous malignant mixed mullerian tumors as described in Guarino et al., 1998, *Tumori* 84:391–397.

Cytochrome C Oxidase (CcO) (SEQ ID NO: 81) is the terminal enzyme of the respiratory chain of mitochondria and aerobic bacteria: it catalyzes electron transfer from cytochrome C to molecular oxygen, reducing the oxygen to water (Michel et al., 1998, *Annu Rev Biophys Biomol Struct* 27:329–356). Cytochrome C oxidase is a member of the superfamily of quinol and cytochrome C oxidase complexes that are related by a homologous subunit containing six positionally conserved histidines that ligate a low-spin heme and a heme-copper dioxygen activating and reduction center as described in Musser and Chan, 1998, *J. Mol. Evol.* 46:508–520. Cytochrome C and ubiquinol oxidases are membrane-bound redox-driven proton pumps which couple an electron current to a proton current across the membrane (see Karpefors et al., 1998, *Biochim Biophys Acta* 1365:159–169). Analysis of mutant forms of cytochrome C oxidase is described in Mills and Ferguson-Miller, 1998, *Biochim Biophys Acta* 365:46–52. Nitric oxide inhibits respiration at cytochrome C oxidase, as described in Torres et al., 1998, *J. Bioenerg Biomembr* 30:63–69.

Heat shock protein 90 (hsp90) (SEQ ID NO: 82) acts as a chaperone molecule in association with the glucocorticoid and progesterone nuclear receptors, and has A, B, and Z regions for facilitating these interactions (Dao-Phan et al., 1997, Mol Endocrinol 11:962–972). Levels of hsp90 are reported elevated in active systemic lupus erythematosus (Stephanou et al., 1997, Biochem J. 321:103–106). Increased hsp90 expression is implicated in regulation of forms of cell injury that lead to programmed cell death as described in Galea-Lauri et al., 1996, J. Immunol. 157:4109–4118. Hsp90 is upregulated in regenerating fibers and diseased fibers of Duchenne muscular dystrophy (Bornman et al., 1996, Muscle Nerve 19:574–580), and is a candidate substrate for proteolysis during ionizing radiation-induced apoptosis of some breast cancer cells (Prasad et al., 1998, Int. J. Oncol 13:757–764). Hsp90 is involved in dislocation of the mutant insulin receptors from the endoplasmic reticulum to the cytosol as described in Imamura et al., 1998, J. Biol. Chem. 273:11183–11188, and associates with and activates endothelial nitric oxide synthase as described in Garcia-Cardena et al., 1998, Nature 392:821–824.

Integrin alpha 6 (SEQ ID NO: 83) is in the family of integrins, heterodimeric, cation dependent cell membrane adhesion molecules that mediate cell-cell and cell-matrix interactions. Integrin alpha 6 is a component of the hemidesmosome complex (Jones et al., 1998, Bioessays 20:488–494). Integrins maintain tissue integrity and regulate cell proliferation, growth, differentiation, and migration. (See Thomas et al., 1997, Oral Oncol 33:381–388). In oral squamous cell carcinomas there is a variable loss or reduced expression of integrin alpha 6, as described in Thomas et al., 1997, Oral Oncol. 33:381–388. Alpha 6 integrin also plays an active role in invasion of intestinal and diff-use-type cells of representative gastric carcinoma cell lines as described in Koike et al., 1997, J. Cancer. Res. Clin. Oncol. 123L:310–316.

Osteogenic protein-1 (OP-1) (also called BMP-7) (SEQ ID NO: 85) is a morphogenetic factor (and a member of the bone morphogenetic protein (BMP) family of growth factors) and is highly expressed in kidney and involved in tissue repair and development (see Almanzar et al., 1998, J. Am. Soc. Nephrol. 9:1456–1463). OP-1 is also expressed in the developing nervous system and can induce dendritic growth in sympathetic neurons as described in Guo et al., 1998, Neurosci. Lett 245:131–134. OP-1 stimulates cartilage formation as described in Klein-Nulend et al., 1998, J. Biomed. Mater. Res. 40:614–620.

OP-1 induces down-regulation of insulin-like growth factor binding proteins (particularly IGFBP-5) thus affecting IGF-1 in the context of bone cell differentiation and mineralized bone nodule formation as described in Yeh et al., 1997, Endocrinology 138:4181–4190. OP-1 can be used as a bone graft substitute to promote spinal fusion and to aid in the incorporation of metal implants (Cook and Rueger, 1996, Clin. Orthop. 324:29–38). The three dimensional structure of OP-1 is reported in Griffith et al., 1996, Proc Nat'l Acad Sci 93:878–883.

The protein encoded by SEQ ID NO:56 is a putative secreted protein and is highly expressed in fat tissue.

TABLE 1

Novel Differentially Expressed Metastatic Marker Polynucleotides

| TRANSCRIPT NUMBER | SEQ ID NO: | non-metastatic breast MCF-7 | breast cancer metastatic to bone and/or lung MDA-MB-231 | breast cancer metastatic to lung MDA-MB-435 | low metastatic from colon KM12C | high metastatic from colon KM12L4A |
|---|---|---|---|---|---|---|
| 901 | 1 | − | + | − | | |
| 907 | 2 | − | − | + | | |
| 9102b | 3 | + | − | − | | |
| 9114 | 4 | − | − | + | | |
| 9121a | 5 | − | + | − | | |
| 9129 | 6 | + | − | + | | |
| 9139a | 7 | + | − | − | | |
| 9143b | 8 | + | − | − | | |
| 9157b | 9 | − | − | + | | |
| 9166 | 10 | + | − | − | | |
| 9170b | 11 | − | + | − | | |
| 9190a | 12 | + | − | − | | |
| 9191 | 13 | − | − | + | | |
| 9216 | 14 | − | − | + | | |
| 9224c | 15 | + | − | − | | |
| 9230b | 16 | + | − | − | | |
| 924 | 17 | + | − | − | | |
| 9242a | 18 | − | + | − | | |
| 9259a | 19 | − | − | + | | |
| 9261 | 20 | − | + | − | | |
| 9272 | 21 | + | − | − | | |
| 9293b | 22 | − | + | − | | |
| 9304b | 23 | + | − | − | | |
| 9307a | 24 | − | + | − | | |
| 931 | 25 | + | − | − | | |
| 9313 | 26 | − | − | + | | |
| 9316 | 27 | + | + | − | | |
| 9318b | 28 | + | − | − | | |
| 9320a | 29 | − | − | + | | |
| 9330b | 30 | − | + | − | | |
| 9335 | 31 | + | − | − | | |
| 9337 | 32 | + | − | + | | |
| 9342b | 33 | − | + | − | | |
| 9343c | 34 | + | − | − | | |

TABLE 1-continued

Novel Differentially Expressed Metastatic Marker Polynucleotides

| TRANSCRIPT NUMBER | SEQ ID NO: | non-metastatic breast MCF-7 | breast cancer metastatic to bone and/or lung MDA-MB-231 | breast cancer metastatic to lung MDA-MB-435 | low metastatic from colon KM12C | high metastatic from colon KM12L4A |
|---|---|---|---|---|---|---|
| 9350e | 35 | − | + | − | | |
| 9351b | 36 | − | + | − | | |
| 9361 | 37 | + | − | − | | |
| 9368 | 38 | − | + | − | | |
| 9373b | 39 | − | − | + | | |
| 9385a | 40 | − | − | + | | |
| 9386c | 41 | − | − | + | | |
| 9388d | 42 | + | − | − | | |
| 9390 | 43 | + | − | − | | |
| 9393 | 44 | + | − | − | | |
| 9396 | 45 | − | + | − | | |
| 944b | 46 | + | − | − | | |
| 951 | 47 | + | − | − | | |
| 953 | 48 | − | − | + | | |
| 954a | 49 | + | − | − | | |
| 968 | 50 | + | − | − | | |
| 971 | 51 | + | − | − | | |
| 983c | 52 | − | + | − | | |
| 985 | 53 | + | − | − | | |
| 990 | 54 | + | − | + | | |
| 998 | 55 | − | − | + | | |
| 316 | 56 | + | − | − | + | − |
| 126c | 57 | − | − | + | | |
| 207-4 | 58 | − | + | − | | |
| 265-3 | 59 | + | − | − | | |
| 29B | 60 | − | − | + | | |
| 305B-25 | 61 | + | − | − | | |
| 326B-39 | 62 | + | − | − | | |
| 34B-11 | 63 | − | − | + | | |

+ indicates differential expression as identified in differential display
− indicates absence in differential display For transcript number 316, reverse transcription PCR (RT-PCR) was used to detect expression in the breast cancer cell lines.

TABLE 2

Differentially Expressed Metastatic Marker Polynucleotides

| TRANSCRIPT NUMBER | protein | SEQ ID NO: | non-metastatic breast MCF-7 | breast cancer metastatic to bone and/or lung MDA-MB-231 | breast cancer metastatic to lung MDA-MB-435 |
|---|---|---|---|---|---|
| 902 | osteopontin | 64 | − | − | + |
| 9112 | nip | 65 | − | + | − |
| 9132 | Ca-dependent protease | 66 | − | + | − |
| 9158 | IGF-R | 67 | + | − | − |
| 9174 | ILGF-BP5 | 68 | + | − | − |
| 9177 | lactate dehydrogenase | 69 | − | + | + |
| 9202 | ufo TKR | 70 | − | + | − |
| 9210 | eIF2 | 71 | − | + | + |
| 9212 | glutaminyl cyclase | 72 | − | − | + |
| 9213 | gp130 | 73 | − | − | + |
| 9222 | TGFb-II | 74 | − | + | − |
| 9232 | E-cadherin | 75 | + | − | − |
| 9239 | serpin | 76 | − | + | − |
| 9250 | secreted pS2 | 77 | − | − | − |
| 9260 | LIV-1 | 78 | + | − | − |
| 9315 | GTP-binding protein | 79 | + | − | − |

TABLE 2-continued

Differentially Expressed Metastatic Marker Polynucleotides

| TRANSCRIPT NUMBER | protein | SEQ ID NO: | non-metastatic breast MCF-7 | breast cancer metastatic to bone and/or lung MDA-MB-231 | breast cancer metastatic to lung MDA-MB-435 |
|---|---|---|---|---|---|
| 9317 | vimentin | 80 | − | + | − |
| 938 | cytochrome C oxidase | 81 | + | − | − |
| 9382 | Hsp 90 | 82 | − | − | + |
| 9394 | integrin a6 | 83 | − | − | + |
| 956 | desmoplakin | 84 | + | − | − |
| 970 | osteogenic protein | 85 | + | − | − |

+ indicates differential expression as identified in differential display
− indicates absence in differential display Within the scope of the invention are variants of the proteins described above. A variant is a protein encoded by a polynucleotide wherein the global sequence identity of the DNA, as compared to the corresponding SEQ ID NO: herein, is at least 65% as determined by the Smith-Waterman homology search algorithm as implemented in MPSRCH program (Oxford Molecular) using an affine gap search with the following search parameters: gap open penalty of 12, and gap extension penalty of 1. The protein encoded by the DNA having the sequence identity described above will exhibit the percent activity described in the preceding paragraph.

Also within the scope of the invention are fusion proteins comprising the proteins and variants disclosed herein. Proteins preferably used in fusion protein construction include beta-galactosidase, beta-glucuronidase, green fluorescent protein (GFP), autofluorescent proteins including blue fluorescent protein (BFP), glutathione-S-transferase (GST), luciferase, horse radish peroxidase (HRP) and chloramphenicol acetyltransferase (CAT). Additionally, epitope tags are used in fusion protein constructions, including Histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and Herpes simplex virus (HSV) BP16 protein fusions.

These fusions can be made by standard procedures in the art of molecular biology, and many are available as kits from, for example, Promega Corporation (Madison, Wis.); Stratagene (La Jolla, Calif.); Clontech (Mountainview, Calif.); Santa Cruz Biotechnology (Santa Cruz, Calif.); MBL International Corporation (MIC, Watertown, Mass.); and Quantum Biotechnologies (Montreal, Canada).

The proteins of the invention, and variants as described herein, can also be used to detect protein interactions in vivo, using the yeast two-hybrid system, for example as described in U.S. Pat. No. 5,674,739.

In addition to the ribozyme and antisense constructs described above, the polynucleotides of the invention can be used for inhibiting transcription via triple helix formation as disclosed in U.S. Pat. No. 5,674,739.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

I claim:

1. An isolated nucleic acid molecule selected from the group consisting of:
   a. a polynucleotide comprising SEQ ID NO:28,
   b. a polynucleotide comprising the full-length complement of SEQ ID NO:28,
   c. a polynucleotide consisting of at least 11 contiguous nucleotides of the complement of SEQ ID NO:28, wherein said polynucleotide is a probe for the identification of SEQ ID NO:28, and
   d. a polynucleotide comprising a sequence which is at least 95% identical to the full length of SEQ ID NO:28, wherein said polynucleotide has the same differential expression profile in metastatic relative to non-metastatic cancer cells as SEQ ID NO:28.

2. The isolated nucleic acid molecule of claim 1, which is DNA.

3. A method of making a recombinant vector, comprising inserting a nucleic acid molecule of claim 2 into a host cell.

4. A recombinant vector produced by the method of claim 3.

5. A method of making a recombinant host cell, comprising introducing the recombinant vector of claim 4 into a host cell.

6. A recombinant host cell produced by the method of claim 5.

7. The isolated nucleic acid molecule of claim 1, wherein said polynucleotide is at least 95% identical to the full length polynucleotide shown in SEQ ID NO:28, and wherein said polynucleotide is expressed at a greater level by non-metastatic breast cancer cells than by metastatic breast cancer cells.

8. A method of making a recombinant host cell, comprising introducing the recombinant vector produced by the method of claim 3 into a host cell.

9. A recombinat host cell produced by the method of claim 8.

* * * * *

SEQUENCE LISTING

```
<160> NUMBER OF SEQ ID NOS: 85

<210> SEQ ID NO 1
<211> LENGTH: 142
<212> TYPE: DNA
<213> ORGANISM: Homo sapien
<220> FEATURE:
<221> NAME/KEY: misc_feature
<222> LOCATION: (1)...(142)
<223> OTHER INFORMATION: n = A,T,C or G

<400> SEQUENCE: 1
cacccaagaa ctaagaaaca aagggagaat gtacttttgt agcttagata agcaatgaat      60
cagtaaagga ctgatctact tgctccacca cccctccctt aataataaca tttactgtnn     120
```

```
atttcctggg cctaagactc ta                                              142
```

<210> SEQ ID NO 2
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 2

```
cgcgagcaga caacataatt tatttccaga aaacaacaga aatgaacatc atcatgaata      60
catgaaatcg gctgtgatgt gtgaactgct aagggccaaa tgaacgtttg cagagcagtg     120
ggcacaatgt ttacaatgta tgtgtatgtc actttcggta cctgtgaatg catggggacg     180
tgctgaaccc gaaaaaaagt gcctttccat aaggactgca atanagaggg caatttaccc     240
tggtggtaca cggaacctan attcactcct gccatgcctt gccaatagta anctgcaggg     300
tggaacaaga aatcacttgc tctgggggga a                                    331
```

<210> SEQ ID NO 3
<211> LENGTH: 1112
<212> TYPE: DNA
<213> ORGANISM: Homo sapien
<220> FEATURE:
<221> NAME/KEY: misc_feature
<222> LOCATION: (1)...(1112)
<223> OTHER INFORMATION: n = A,T,C or G

<400> SEQUENCE: 3

```
ccnnnnnnnn ntncntnnnn ncnnnnccnn ngnnnnnctn gcccnnncng ctnnnccccn      60
nntnctnntn gntnangnnc ngaaccgcn nnnngnnnnn acnatnntnn gncgnnnnnt     120
tcgttnnnnc ntgnntccnc nnnnnctngt ncnnnnnggn ggngcgcncc nccnancctn     180
cctcnntgnn ncnnnctnnt nnctnngctg ngtctcncng cncngngcnn nnngggtct      240 nccgtnctnc nnnnncnnng ttttangncn gnaanacgcc cgcncgagct tttagccatg     300
ggggataacc gaaccaaacn tnacactctc agaggatcca cctntgggtg caagcgaaac     360
tngancnatc tatactctcg anggtncaag gacattgntg agagaaatgg anncacagcc     420
cacgttcatt gggtangaga ctccnattaa natttctgtc tccccngatg ggccctagac     480
ccatgaatcc ctattangat cccntcagcg gccanacncn gtggctccnc ctgtaatccc     540
ccacntcggg aggctgatga gggcgaatcc aaggtcagga aatntatata gacncctggc     600
taaccggnga acccccctc taaaancaaa aaaaaannec nncnngtntt tanagggngt      660 tnttttcnt cgccncgccc gncncgnccg cttnctngct ccncctgnnc nnncntccct      720
ncnncnntgn tcanccengc gnnncgennc ntnccttnnt gngtctggtc ncncttcnnc     780
ctctcttncn ccnntgtccn tngctctcag ccnctgcccc ncctnnccn tnngtgnnnc      840 cnccntnatg nccncncnan aggngcangc nntggcncgc tgnccnntgt ntgtcnctcn     900
acgganantg nactcncnac tnngnnacgc natnnnanct ctgctctcag atgacagcan     960
cggnntnnnc ngcctctanc nncgnnnncn nagccnncga nnnaggnanc cgcgntcant    1020
cnnntttcnc tctncnntg catntctgat ngccgtgnct ncctcnnttn ctcnagcncn     1080
tnnccacctc tcgtttangc nctnnncnna nn                                 1112
```

<210> SEQ ID NO 4
<211> LENGTH: 183

```
<212> TYPE: DNA
<213> ORGANISM: Homo sapien

<400> SEQUENCE: 4
aaaactatga attccatact tgaggtttcc cagccaattg ctcccttctg ctttagaagt      60
gactaggtac tgagagtaca aacactccca ctttataatg aaggcgtcat gtcacccctt     120
cctttacagg tcctggggtc caggagaccc agaatgaagg tgtcagttgg gcatgaagtg     180
tta                                                                   183

<210> SEQ ID NO 5
<211> LENGTH: 1092
<212> TYPE: DNA
<213> ORGANISM: Homo sapien
<220> FEATURE:
<221> NAME/KEY: misc_feature
<222> LOCATION: (1)...(1092)
<223> OTHER INFORMATION: n = A,T,C or G

<400> SEQUENCE: 5
ttncagacca agaagacttg atnagctgaa acccattgcn ctacttggaa ngtgatcngc      60
aaaagctgcc tcagtcanac accggggata aatctggatt tgggttccgg cgtcaaggtg    120
aanatnatac ctantaanga acnctgtaca ntgccncaag cangtganga ccncccacga    180
gtttacatna atacaatnct gaaacnacnc aggctggttt tatatctaca tatttgactt    240
accactatcn cantaaagtt tngcacctt tcccgaacga aaanaacccc ccntnntgnn     300
ttcttttnaa aanaccntng nnccncnttn ccgtcncncc ccnnatantn nncnnatccc    360 ccctctncc nntccntnnn cgtaanngc gtngcttntg cngtntntgt cccgttttcc     420
tccgcttngt cntttntcta tatnggctnn tnttatnccn ngcccttcgt cncctnnngn    480
ttcgtctgtn cntagtcctc ntnctngagc cccanttgnt acttcnngct tcnnctccgc    540
attccntctc cgcncnnanc ncnnntctca nannatgnnc nntnnctncn nccnatncnc    600
cctnanagnt tcgnctagac cntcnacntt gtntcccgnn ctcttagngn tctgctncta    660
gtgtntnnct catctcctct ncttctctct cctttgacnc ngnncnctcc atcntnntct    720
gnctttctca tcncnnnnng cccctncctcn cnnagtntgn gtgcncnnnc ttnnnntcna    780
nctngtcgcc tccgtttcn actnnnnccn nngcngnncg nnngctcttt ctntcnntta    840 gactnaccctt ntctgnnnnn tcannctagc nctgtccntc tctnnctgc atcnttanac    900 atcttnntcn cccnctcgca ncntnctntt nacnctcnca tacgttnccn nnctcagtcc    960
gcagnnnngt tncntncngt cntctcgcgn ctcnnntcct ctctnnnacn cnctggtct    1020 ncgnctcgct ccnncccatn cntncctcgt tgntcnnnnt cnnatacgtn tncangccnc    1080
ntctctccnc tn                                                        1092

<210> SEQ ID NO 6
<211> LENGTH: 504
<212> TYPE: DNA
<213> ORGANISM: Homo sapien
<220> FEATURE:
<221> NAME/KEY: misc_feature
<222> LOCATION: (1)...(504)
<223> OTHER INFORMATION: n = A,T,C or G

<400> SEQUENCE: 6
ctggagcggg atcatttana atactttaca gatatntgca ccaggtacat ntatntgcgt      60
ccattggtag cacagctgag acctgtgtct cacatcagcc taggtgaagc ctactacaaa    120
```

```
taatgccaag ggagaanagc cagtacacta tatggtttat actctttatc cctttattca      180
tagcatgttt tttaaaaatg ttatattatg caacagatgt gaggcagcan ctaagctata      240
cttaagaatt ttctctcacc ttccaaacca aagtgtcctg aataagccag gagacttat      300 cttttgtgca ccctggtgca catctgactg ttgtcctanc canaaactct ctgaggccac      360
tgaaagaaca gtggccctat cgatttcatt cctaggtctc aaaaatacna tgtngccttg      420
taacataatt agggacagca cctctatttc acaattataa tctaaggtag gataagacga      480
cacagcagca ataaacttac aagt                                             504

<210> SEQ ID NO 7
<211> LENGTH: 1132
<212> TYPE: DNA
<213> ORGANISM: Homo sapien
<220> FEATURE:
<221> NAME/KEY: misc_feature
<222> LOCATION: (1)...(1132)
<223> OTHER INFORMATION: n = A,T,C or G

<400> SEQUENCE: 7
gcgngccccc tngtngnncn ttntncncng ttttctgctn tntttatnng aggnctnggt       60
nnttnntctt agggnnntng tncggtcnng ttnntgttnc gagcagaaag tgnatatttc      120
atgcngccaa gcttntttat tgaaaantcc taattntatt gnccgtntag taacatgttt      180
gttcnacaan gctaatttct nataaancaa aacacannnt tttcttataa gtngtataaa      240
ttatttnatt tacagaaact tgtttcaaaa canatgnact anntatttct nctcttttaa      300
atanccanac taattttcta tccctngaca tctgttcatg ttctatncag cagccaacac      360
aaagtccanc tgagagctct tgattaangt gtncgnatta tctagctact tccnacgttt      420
tnggngcnng aaatgncttt taananncctg gcctcaaaaa anaaaaanan cccccgnnn      480 agggnnttc cntntanaaa aanggntcnc tcnnccngtn ngagactgtc tccctgnntn      540
ngnnnntcgc tntnatcang ngccncnang ctcnccntcn ctnnngcatt ngatnnntan      600
cnnnctgaga tgngnntang ctgntncntn ngtgtcntan gtctcgacgt tgnntggntn      660
tangnancgn cnntntnnnc nnattgncga gngnntaagt gtgctcttct cntnacntct      720
ntcnnnancn tctnngatgt tnatacggcc gtgcttnctt atcnntgana ncgntctnan      780 nannntncgna tgagnntnta ctgcncncnt gtgtcatctt tctctctant gtgtnctnna      840
nncnngtnat tncgcnnnac tgntantnag tggtatnnag anntcgnncg cnngngccnn      900
tttnnctgtn gnnatnagnt ntcanganat tnatncnntc tncgtgatag anagntnagt      960
gnnggntctg actgatncgt gtcctagtnn cngtgacatc gnncgttann gtcngcactc     1020
tagtanannt nagtnngang ntgtanatnn ntctcntgtt tcagtnnagn cccncgagcg     1080
cntcanntnt nantgtctcn tctnngtcgt anncntgtcg agtngtnana nn             1132

<210> SEQ ID NO 8
<211> LENGTH: 736
<212> TYPE: DNA
<213> ORGANISM: Homo sapien
<220> FEATURE:
<221> NAME/KEY: misc_feature
<222> LOCATION: (1)...(736)
<223> OTHER INFORMATION: n = A,T,C or G

<400> SEQUENCE: 8
ntgggcccga cgtcgcatgc tcccggncgn catggnnnnc tggtttggtc anatgtgaat       60
aacgnagaan tgagaccacn ganaagaacc acantgtnan ggnncttgca cntgntanga      120
```

| | |
|---|---|
| antnagnaat gccttttnc tgagggcntt nggnnntcat nnangggngt gnggnggntt | 180 |
| ncacctgtaa taccaccact ttncnatgcc actgccngtg natcaccngn ngtaaggact | 240 |
| tcaanaccag ccttatnaac ntgggnaaac cntntntcta ctaaaaatnc tnnaantatc | 300 |
| tgngcnnngt ngngcgttct tntannnccn gctgnacnng angncngngn angntantcg | 360 |
| cntgaacntg ncntgttana gtngcantga gcctaaatca cantgatgta ttnncatctg | 420 |
| ggacgacacg ancngacgac tcncgtactn aaaaaaaaaa ncccnttnng gggggtttt | 480 |
| tnnnggtatt anntatantt ggagaantt gggtcannng aatattntta catgaaaaat | 540 |
| naggaataac tntatntgtg tacattgggt tnnaaanang acantantgg nnctaaactn | 600 |
| ttnggggngg agggnnatt agggnnttaa ttnggnnnct tnnaaanncn nntnnngtat | 660 |
| nanaanantn tttnnanaag ngnantngnt ttaaancctn aangnttnnn tnctnttann | 720 |
| ttnnaannnn anannn | 736 |

<210> SEQ ID NO 9
<211> LENGTH: 690
<212> TYPE: DNA
<213> ORGANISM: Homo sapien
<220> FEATURE:
<221> NAME/KEY: misc_feature
<222> LOCATION: (1)...(690)
<223> OTHER INFORMATION: n = A,T,C or G

<400> SEQUENCE: 9

| | |
|---|---|
| tnnnccctggn tggtcactcc cttctgtcct gttagctcat ggtgtaagat gatgtcttgt | 60 |
| cagtattact gttttgctaa gccgcttcat tcatgcctac acaattttt tttaaaaggg | 120 |
| aactttagtt aattaagtga tagggactt aaatatgaat tanaatggtg cagaaagaga | 180 |
| taccttttct ggatatttta aagtttaaag gtcantttct cttaatctga ttatgtgcac | 240 |
| atatgaaaat ggcacatcat atacatgtaa aatcaggcag tatncattta ttaattactg | 300 |
| tatttgacaa aggaaactct taaattataa tgtgaaacct ggttttatga aaccaatgac | 360 |
| tagtgcanca tttcagcata tgcaaaaaaa aaanncctnt tggngngctg tttacaaagg | 420 |
| aaattgttgg atttcacgat ggtttcagga naanaaggtt ttcntcatcn agggtaaacn | 480 |
| tcccggataa ggcntngntt taatntnntt annccnnccn atngntaann gtggaaatta | 540 |
| ancctctgaa naaaanancc cacntnnttn gccttgggct tnantctntt tggcngnanc | 600 |
| naaaggnnct tnccaggtnt cntgnngggc cngnngaann ataannaann ngggnnctt | 660 |
| nggaaacctt ncnnnaanan tncccnccc | 690 |

<210> SEQ ID NO 10
<211> LENGTH: 395
<212> TYPE: DNA
<213> ORGANISM: Homo sapien
<220> FEATURE:
<221> NAME/KEY: misc_feature
<222> LOCATION: (1)...(395)
<223> OTHER INFORMATION: n = A,T,C or G

<400> SEQUENCE: 10

| | |
|---|---|
| tggtatctga cnnaataaga atgcacccat ttgtgagggg taatatttat ctcangattt | 60 |
| actgtaaata tgtatacaca catacaaaaa cccaggcatt gttaagagaa aatnatggcc | 120 |
| cagaggttna aattatcaga cagaaccttt aanaataatt atgattaatg tgttaaaatt | 180 |
| ctagtggaaa agataaaataa catgctcagg anattttagc anagagatag aaactatntn | 240 |

-continued

```
ngaagctcaa atgaaaatgc taggaaatga aaagcagtat tggaggtgaa agattccttt    300
ggcaatttat caacanactg gagatggcan aggcataatc agtantattg aaggcagatt    360
actatntatt atncaancaa aaaaaaaaac cccct                                395

<210> SEQ ID NO 11
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 11
aacgaggccn ngaggccaat gaggccaaca agacgatgcc ggagacccca actggggact    60
cagacccgca acctgctcct aaaaaaatga aaacatctga gtcctcgacn atactagtgg    120
ntcgctacag gagggaacgt gaaaagaaca tctccagagg aactggtgaa tgaccacgcc    180
cgagagaaca gaatcaaccc cgaccaaatg gaggaggagg aattcataga aataacgact    240
gaaagaccta aaaagtagca agaagctaca tccctcaaac ttcggcaatg aaaataaagt    300
ttgagaagct caaaaaaaaa aanccctttt g                                   331

<210> SEQ ID NO 12
<211> LENGTH: 693
<212> TYPE: DNA
<213> ORGANISM: Homo sapien
<220> FEATURE:
<221> NAME/KEY: misc_feature
<222> LOCATION: (1)...(693)
<223> OTHER INFORMATION: n = A,T,C or G

<400> SEQUENCE: 12
tncaacgcgt tgggagctnt nccaaggtgg nctagcnnca ttaatgccct accgtgggaa    60
tatggntgaa gatcttgact aggggactta tgaacccatg cagccgtgcc caaatcctac    120
caaactgacc ttactttctt gaagacggaa ttgtagtatg gtcgagctca tgcttttgt    180 agtaggccat ncaaattcga ttgactggct aaaaaagatt gttagtggag ctggaagaa    240 acattttggc tgatgataga tgaatagagc ttggaacaat caaaaggaaa agcagaaagt    300
ctatacctat tcataagaaa aagttagtat gtttaccgaa cattataaa gaattatgac     360 attttcaaag ttttaaaatt ttattttgta gggacggggt ctcattgtgt agcccacnct    420
ggtctgtttc ttgaggattt actatanact gggctgtatt caaagcattg gggatacagg    480
catgaatgag cccccattgc ctgaacttac cattcaatct gggcagtgaa agaanaggga    540
tgntgggaga nccttacaaa gatgaaatgt cgctaactgg agaaatccct actttcagtc    600
agactgaann ggaacaggta gtnactgtgg gtagccctct ttgggnangg gtngattttc    660
cacatgtgcc cagttaaggg ccnagaacat taa                                 693

<210> SEQ ID NO 13
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 13
ttggtatcng gggatggggn agggagata gncccgaagc atcccnnatt ctcagtaaac    60
```

```
tccttggnat canannatat cntggccnaa gaaccncnca ccntctntgg gttagaaata      120
ccgctntatn ngtatgagg ggatngggcn tacgnnataa tttnctatng ganggtattn      180
ccgcactant gacnagttct ttctnnggtc catttnnaac nacantnttg acattgntga     240
tctgcaannc tgtaaaatag tcttncagtg ggcaatnnnt gcacaactgg gttnggtntc    300 anaca                                                                 305

<210> SEQ ID NO 14
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 14
agcagacaac ntaatccaag ccatttacca aataantata tgcgatgcac attgaatcct     60
ggcgctctag atatantgcc ccaaaggaaa gagnacaaag tnttccnccc ntagttctac    120
natgnctatc cnctatcacc tnctgnttcn naagntttnt aaaaataaat tctcttgtat    180
ancatccnat atcncaccgg tccaaagcgc aacaatctgc aattcanaan ttccaacaat   240
cnatntatgn actttcntag gtccggtgtt ctaanatnta atattctaac acttactctc   300
agatctta                                                             308

<210> SEQ ID NO 15
<211> LENGTH: 304
<212> TYPE: DNA
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 15
ngtnaaggga tatttattcc tgttttaaaa ggatacaacc aaggtaggga aggcttcgtt     60
attggtgatt attcagaaga cctatttttct ttacatatgc tatggaaaca atactgtttt    120
ccgctacaga atacagttta tgattatact tttgtaaatt gcctgctttt ccctgtcat     180 ctgctaattc caatttgata ctgttctgtg ttcaaaaata cagcatgagc aagctgtaat    240
ggtgcctgtc gagagtccca gctgcttggg gggctaaggt gggaggatca tttgagccca   300
ggag                                                                 304

<210> SEQ ID NO 16
<211> LENGTH: 703
<212> TYPE: DNA
<213> ORGANISM: Homo sapien
<220> FEATURE:
<221> NAME/KEY: misc_feature
<222> LOCATION: (1)...(703)
<223> OTHER INFORMATION: n = A,T,C or G

<400> SEQUENCE: 16
ccggtngnct aaaaggacc agcctaatgt agaaggtggg tatttggacc agaggcttta      60
gattattatt ttagatccta catatacttt tatcagtaga atgatttcat tnagatgtat   120
aatgaaaaag ggtaatgcaa aaattatgta atagatacca aattagggaa gtttggcaat   180
ttcaatggca tatttttagt caaggnacac agatggcagt gccataagca agtctataaa   240
```

```
tatcggctgc agccatcccc ctcattttaa atgttgccct aataatcaat gcagttaaca    300
agtatattgg ctgtgtgtca tgaaatagtt catgttcaga tggaaatgtt aggttactgt    360
atggtttatg gagattaatg aaaatgaatg cccaaaaaaa aaanncnttt tngnggnggg    420
tttnnnangn acngggctgg attcaaanca ttggggatnc angnttnaat gngncnccat    480
ttgnctnaac ttaccttnna nnntgggcnn tnnatngaan angggatnnt gggannaacc    540
tttnnangnt nnaantgtnn ncttactggn gnaaannncc ntaantttn nnnntnnnnn     600 ngnaaggggg naannnnnnn ntnancttnt gggggagncn nttntggggn anggggggnt    660
nnttnnnncn tnnnggccnn nnnngggggcn nnaaantttt tgn                     703
```

```
<210> SEQ ID NO 17
<211> LENGTH: 171
<212> TYPE: DNA
<213> ORGANISM: Homo sapien
<220> FEATURE:
<221> NAME/KEY: misc_feature
<222> LOCATION: (1)...(171)
<223> OTHER INFORMATION: n = A,T,C or G

<400> SEQUENCE: 17
```

```
tccgcntcta agtaattcat caataacgca tgtccactta atgtgaaaat tggtaccatc     60
taatanaatc ttcaacatgg cnatccacnc tattccaata atgaaatgca aatttccctg    120
ccttctttac tanggtcatt tntagattct tgaggaatga gttctactct t             171
```

```
<210> SEQ ID NO 18
<211> LENGTH: 689
<212> TYPE: DNA
<213> ORGANISM: Homo sapien
<220> FEATURE:
<221> NAME/KEY: misc_feature
<222> LOCATION: (1)...(689)
<223> OTHER INFORMATION: n = A,T,C or G

<400> SEQUENCE: 18
```

```
antnngcttn ggtactaagc agaatcactt ncttgggaac tccatgtaac tngtggcttt     60
tgtgattgaa atagcatcag taaangtctg accctgtggt aaagacacat atgngcgtgg    120
accnggctat gtctgacttt gtgctgctca ggacactctc tgtnaccaaa agngagagan    180
cctggannac ctcanggggt canatgtttg aaggagctgc tgagtatcct ggcaggcanc    240
anagccttac catcagtttg ctgcatggaa ggctgtgtgc ctctattcc ctgctatttg     300 ttgaactccc ttgagctccg gtccttccta agtgagagag atgatcccaa tagcnccaac    360
ctgagagggc tggggagatg ttngaaggaa agcttggctg gggagctgaa tctgcctgt     420 ggtacatgct tggtaactgg tggccaggan acccgggngt gtgtnctggg actgtcncac    480
tctgctgacc agggtattga agtccccnc tcaaanacac agaatntntc tgaccaaggg     540
tangtatgan atgacntgtg gagcactttg nataaactgg ttctcatngg nggtcccctt    600
gaanaggtgc tnnatctgtt caaaaatacg tggctgagct ntanacccng natcctctgt    660
cagagacatg ggcagggga ctcaatgct                                        689
```

```
<210> SEQ ID NO 19
<211> LENGTH: 721
<212> TYPE: DNA
<213> ORGANISM: Homo sapien
<220> FEATURE:
<221> NAME/KEY: misc_feature
<222> LOCATION: (1)...(721)
<223> OTHER INFORMATION: n = A,T,C or G
```

<400> SEQUENCE: 19

```
tatanatact nngctatgct ttctaccctg tgtgcctgga gacctactat ggaaaaanga      60
tcagccacct taccttctac tgggtacctg ctgtgagtct gcctatgcca caacgattaa     120
tganggaggg gtacccaagn gacaaanccn acatgccgct tacagccccc gttggatngn     180
tgctcattca acagtcttgc attcagtagg tgtttgacat cacctactat gtgncaggct     240
ctatgctang nactggggat acaggagaga ntnaagcgta aagtctttgg tctcaaggaa     300
tttgcattct agaaagtcta agatgtaata aatgtactgt gggacatgtt aaataagtgc     360
tataacgaaa tataaagggt ttgggagcaa aaaanaaacc cnnttgtggg gntctntncc     420
nctctgatga agcttactta cttttaacct tnccttctcc tttaaaggtg tttcctggtt     480
cccctttcct ttacagattg gttattggtc ttgctgagga gtaggactac aattnccagc     540
attctnctgg aagccaaagc tgtgctacaa ttgnnccaaa gaagatngta atcttaagcg     600
cccntaatgg taaaatngta ttaaaangtg gacctttgac aaataaattg nttcgatttc     660
ngaattccgg gttngnagct tngngntncc aaaaaccctt nggggntccc ttttgggcac     720
c                                                                    721
```

```
<210> SEQ ID NO 20
<211> LENGTH: 248
<212> TYPE: DNA
<213> ORGANISM: Homo sapien
<220> FEATURE:
<221> NAME/KEY: misc_feature
<222> LOCATION: (1)...(248)
<223> OTHER INFORMATION: n = A,T,C or G
```

<400> SEQUENCE: 20

```
cttaaacacc ccncccatct ncncccaga atgagntaan catactcntc nntactgnat      60
ctccgtatcc gtccctacnc nggnttgtga ggtgtcatta gcngatatta ctcctcatcn    120
ncatcntgan cannatcccc catcnnccat atgntgatna nnacaaacca tnctattncg    180
ccgnngaagc cnntcnnttc attggattcn tagaccgcan angtcctnat tcngacacng    240
aatcggta                                                             248
```

```
<210> SEQ ID NO 21
<211> LENGTH: 298
<212> TYPE: DNA
<213> ORGANISM: Homo sapien
<220> FEATURE:
<221> NAME/KEY: misc_feature
<222> LOCATION: (1)...(298)
<223> OTHER INFORMATION: n = A,T,C or G
```

<400> SEQUENCE: 21

```
ggtctaaggg atgtgatgng agcatagaat ttanctntat ggncatanta gggacatntg     60
ctgatntacn tggnctgcgg tcnntgaaag gtggngnatg atgactgatg tcatnagtag    120
tacnanggac tncgnnanct gggatcnggg nttacnttgt tcatngtnag agtgnnancn    180
aagtanatgn taggnataaa gatgttncgg gagatgggtc tacaaantct tttnaagatg    240
ntcatcttga ananntatcaa gtgtgnttgg tataatgact atcattatac aatgtcaa     298
```

```
<210> SEQ ID NO 22
<211> LENGTH: 591
<212> TYPE: DNA
<213> ORGANISM: Homo sapien
<220> FEATURE:
```

<221> NAME/KEY: misc_feature
<222> LOCATION: (1)...(591)
<223> OTHER INFORMATION: n = A,T,C or G

<400> SEQUENCE: 22

```
tcgctagant actattcggc cgcaacgggg agcctgatga ggacgcttat gatatgagga    60
aagcactttc cagggatact gagaagaaat ccatcatacc attacctcat cctgtgaggc   120
ctgaagacat tgaataaccc tgggcagtgg ttcttaggca gatactctag atgctttatg   180
gacaatatta ttttcattgg atgattctgg agctctatta ggagaaaagt aatcatttta   240
ggtcttaaag acttcaagaa atacaggtt  atcaatttat tttaaatctc attgtttcca   300
gttagcaata tcatacctat taaagctgtt cattgtaaca aaattcaatc aaaaaggcag   360
ctaggtcaga aggaaacata ccactctcat ggttcatagt attcactgta tgtatgctag   420
ggaaaagact tgctccagtc tcctcctcag ttctgtgcct gagaaccact gctgcatata   480
tttgttttta aattttgtat tgaactgtta attgaagctt taaaagcata tatgaaatgt   540
ataaatctaa gatgtataat acattattga ctccaaaaaa aaaaacccct t            591
```

<210> SEQ ID NO 23
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 23

```
gnnnnnngtt nnnnagcngg ttnggtncng actcccnttt atnatgaggg acactgaggc    60
ttcaagagat taggagactt gttcaaagac acacagctgg taagtgatgg aggcaggatt   120
taaacctggg tttcactgca tttcccatca ctggctttta gccatgatgc tctactgtgt   180
aaccctctta attcttgacc tgtggctata agtatgtat  tgagagacag gccctccctg   240
agataacttt ccagccttga caaaggcaca cccttggttc attccttgga gtgtaggacc   300
tagattgtga caagcccaga tgagtgtgtc tggcagaggg gagcagatct gaggccacca   360
tatgtgttca cctagcccta aggagtgcca gcttcgctgg tatttgtaca gcttccatca   420
ggactgctca ttggccacgt tctttcctct ccctgccacg ttgattaata ctcacataaa   480
ttaatgctca cattagtgtt caagtatgca atgagtgct  taaatcatc  actcacacaa   540
tgaccagact gaggatataa cacacaagag cccctctcct ggtaacccca caatcatgca   600
gatgtgttga cttctctgca ttaccagtct ggtaggcagg gggatatgac agttagaaac   660
agtctttcan acagcagttc tcaacaccag gtcccttgct gcacaatcga atcacctggg   720
ggtttaaaaa aatatcatgc cagtcagcca cnntt                              755
```

<210> SEQ ID NO 24
<211> LENGTH: 513
<212> TYPE: DNA
<213> ORGANISM: Homo sapien
<220> FEATURE:
<221> NAME/KEY: misc_feature
<222> LOCATION: (1)...(513)
<223> OTHER INFORMATION: n = A,T,C or G

<400> SEQUENCE: 24

```
ctttctaccc aacaagcata gaatatacat tgtatacatc agaaacacgg gacattctcc    60
aaaatagacc atatgatagg gcacaaaaca agtctcagta aatttaagaa aatcagaatt   120
```

| | |
|---|---|
| atatcaagta ctctctcaga ccacagtgga ataaaattgg aaattaattc cgaaaggaac | 180 |
| actcaaaagc atgcaaatac atggtaatta ataacctac tcctgaatga ttgttgggtc | 240 |
| nacaatgata tcaagaggga aatttaaaaa ttctttgaac tgaacgataa tagtgacaca | 300 |
| gcctatcaaa aactctggga tacagcaaaa gtggaggtaa aagaaaatt catagcatta | 360 |
| aatgcctata tcaaaaatct gaaagagcac aaataaacaa tctaaggtca ccctcncaga | 420 |
| attggagaaa ctagaacagt ccaaatccaa acccngcaga agaaaagaaa taaccaaatc | 480 |
| cgaacaaaac taaatgaatt gaaaaaaatc ccc | 513 |

<210> SEQ ID NO 25
<211> LENGTH: 574
<212> TYPE: DNA
<213> ORGANISM: Homo sapien
<220> FEATURE:
<221> NAME/KEY: misc_feature
<222> LOCATION: (1)...(574)
<223> OTHER INFORMATION: n = A,T,C or G

<400> SEQUENCE: 25

| | |
|---|---|
| cgatccaaga gattagaanc ccntggagtg gagcatgctt cnctanaatn ccacctgatn | 60 |
| cttggctnaa nacantnngc tctantttgc tttgtgcccg tccacacaan ctaaaaacaa | 120 |
| gggatggggg gaccncnagt gtctaatatn cntaatatcc ntccncnggc aaatgaatac | 180 |
| tttttacaca cttgtannt ntggagggan ggggtnatna tgaggggaan gggaaaggat | 240 |
| gaggagaaat ccaggatnan angtctcttc gtcctctcna gactncctca cactctntgt | 300 |
| ggtnaccngg gttcgttntg tccaatggca gacattatac tccatantct acccnggctt | 360 |
| nntcgggttg ggacgccann actcccccna gtngtnnccc ccnancagcn atacacaagt | 420 |
| ntgaacgggg tttgtggcca ntcatcgcaa tgaccttntc ctcnactcna agaaaantaa | 480 |
| accccttccc ccngattggt ttctaaatct ttcaccccat ctaaaataga aagcnctnag | 540 |
| tgggangggt tnatccccc nttaccntta aaac | 574 |

<210> SEQ ID NO 26
<211> LENGTH: 185
<212> TYPE: DNA
<213> ORGANISM: Homo sapien
<220> FEATURE:
<221> NAME/KEY: misc_feature
<222> LOCATION: (1)...(185)
<223> OTHER INFORMATION: n = A,T,C or G

<400> SEQUENCE: 26

| | |
|---|---|
| gnacnattgg caatgacnga aagaatttga angatgnaca agtnaaagnn acagtggcaa | 60 |
| agaatcttcn gggcgcgtca aaacaattgg gtgnattaag dacaanctcg gtcancagta | 120 |
| taanctctct ttcncgngga ttantngnca taatcatnat tctgacnngt aggacattnc | 180 |
| caacc | 185 |

<210> SEQ ID NO 27
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 27

```
ttctggggct ctatacaggc tcctatttng atccangcgt gctgatgagt gcacagcacg    60
atcacatctg gaaaccacca ntaccaccac cactacgcac ntcaccaaaa ctgtganagg   120
gggcatttca gagacaanaa ttgaaaancg aatagtcntc acgggggnat gcanacattg   180
accatgacca ggcgctggct caggcagnta aagaggccan agatcaacac cctgacatgt   240
cngtgaccag agtggtggtc cttacanaga                                    270
```

<210> SEQ ID NO 28
<211> LENGTH: 758
<212> TYPE: DNA
<213> ORGANISM: Homo sapien
<220> FEATURE:
<221> NAME/KEY: misc_feature
<222> LOCATION: (1)...(758)
<223> OTHER INFORMATION: n = A,T,C or G

<400> SEQUENCE: 28

```
tgctaggtan aaagttacct ctaagggaag ctctgcagaa gaaatcagtg aaatactctg    60
aaagccgcaa ttacaatcaa gaggaaccta cttccctcct ggcaaagaaa cccaaggaag   120
gcgagcggaa gatttacttg gcaattgaaa gtgccaatga actggctgtg cagaaagcaa   180
aggcagaaat caccaggctc ataaaagaag agctgatccg gctgcaaaat tcataccaac   240
caacaaataa aggaagatac aaagtcttat agacatccgg aaaaaagatt tttacctgtg   300
ctggtctatg atgtatgtgg cagttgctgt ctgcagttta caatgtattg tnaatgaaga   360
ttttttaaat tctatcttgc tgatttttt taaatataaa aaactggtac ttggtaaaga   420
aatctgtccg taattncccc ccaatcagtc caactatatt taaagccacc tgttttcnaa   480
ttttgatntc ctttaatgtt nactccaata tccatatttt aaatgtcccg gataatatcc   540
caaaggttta aaaatggaa atntttgaac ttcnnttgaa nanaataaat tcccatcctt   600
tangggntnt cccctttnccc gttcttccaa gaaatgtgac cttccccaaa aaagntnatc   660 cctancttt tgnttccccc ctganttct ganccggac antnacggt taaaanttt   720 ttaaattttc caanncaaaa aaccntntnn tttttna                            758
```

<210> SEQ ID NO 29
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 29

```
ctgctaggta ntaanattat ggatccacat tgtnctgagg anacgaaaat acttgctgct    60
gatngaggtg aaaacgatat tgatccntct ggggttttac ggtgtgcact gggtgctgca   120
cnnacttgtc aaggtttgnt acgtcctctg ggcatctgca aaaggccctg ctctctggag   180
tgttgtatgt agtgtaccaa aanagtattt atacatccca ccaatcaaaa cacagctttn   240
ttacctcatg cgaactcatn caaaccaata gaatntcaac atgttctgta ccttanagtg   300
ctcacttact acctctgaac natactcacg ctgtnntttg tctcttncctt atcttttgc   360 ntcttgtaat taactctttg tttccccttca tcaaatgtaa tgtanatcgt gatctattaa   420
aanaaaaatc anggttgcac ttgctacttt naanaaaccg antgtggaaa cattgggtct   480
naattcacac aggatcngta naactgttgt ggatactgag aaacntttga atgttcctcc   540
ccttattacc atcccgcaaa aaacccctn tnntttt                             577
```

```
<210> SEQ ID NO 30
<211> LENGTH: 449
<212> TYPE: DNA
<213> ORGANISM: Homo sapien
<220> FEATURE:
<221> NAME/KEY: misc_feature
<222> LOCATION: (1)...(449)
<223> OTHER INFORMATION: n = A,T,C or G

<400> SEQUENCE: 30
tttacccaat aanntatagg cgatagaatt gatacctggc gcaatagata tagtaccgca    60
aggganagat gaaaaattat aacnaagcat aatatagcaa ggactaaccc ctatnccttn   120
tgcataatga attaactaga aataactttg caaggagagc caaagctaan accnccgaaa   180
ccagacgagc tacctangaa cagctaaaag agcacaccg tctatgtagc anaatagtgg    240
gaagatttat aggtagaggc gacaaaccta ccgagcctgg tgatagctgg ttgtccaaga   300
tagaatctta gttcaacttt aaatttgccc acanaaccct ataaatcccc ttgtaaattt   360
aactgttagt ccaaagagga acagctcttt ggacactagg aaaaaacctt gtagagagag   420
tcataaaaaa aancccctntn gggnnnngn                                    449

<210> SEQ ID NO 31
<211> LENGTH: 500
<212> TYPE: DNA
<213> ORGANISM: Homo sapien
<220> FEATURE:
<221> NAME/KEY: misc_feature
<222> LOCATION: (1)...(500)
<223> OTHER INFORMATION: n = A,T,C or G

<400> SEQUENCE: 31
tcntggaccc nggtccccnn gngancaaan aagaagggcn ngnttncatn gaaaanccctg    60 tgattntcgc cccggtncag gtgttnannt atggcccncn cncatctggt atacgccnaa   120
acaatntant tttacaatnn gtncccncan aaacaangtt cgtngnnttn actaggtagt   180
taatcccncc ccatgttcaa ataaagggcc cgcgntncna ataaggaanc cnccccgant   240
ggggtccccg aggccctctc cttcataaaa nncattcaac ttccctcccn ctannaaagn   300
aattnttcna atttttnaaa cactccctgt ccangggac tttncccca ntanctgaaa     360 aaatngcntg acgttcccct tcggcctaag ggcnaactt anttnncccc caanacccgn   420
gggnnaggnn naaactcccc tngaagggaa cnactcgcnt aaaaanggaa taatcnccc    480 cnaattattc cctncccggg                                               500

<210> SEQ ID NO 32
<211> LENGTH: 426
<212> TYPE: DNA
<213> ORGANISM: Homo sapien
<220> FEATURE:
<221> NAME/KEY: misc_feature
<222> LOCATION: (1)...(426)
<223> OTHER INFORMATION: n = A,T,C or G

<400> SEQUENCE: 32
gtctatgatc acatctgacg ctattcctat cccttcctc cccgggacct tttcccttc      60 ctccctggga cctttttcccc ttcctgtttta anaanccagg gctgcctgga ggaagctttg  120
tcagatctag tggaatgtga cctccctgga atatgtgccc aggggtttgt ctaagcagtt   180
tcaggctatg gcctttactc catctggtcc ccatccctct tatctctctc atgtgtggct   240
```

-continued

| | |
|---|---|
| gcacctggac gcttggacca tagctgtcac agcccctgg ggaggaaccc actccttggc | 300 |
| catntcagcc tgtgcaatgc aaggctcttg tttgatctgt gtgctgacan aaagcccagc | 360 |
| ttccttaaga acttttcatg tggaacactt tggttttgan aagaaaataa atcanaaacc | 420 |
| attaaa | 426 |

<210> SEQ ID NO 33
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G

<400> SEQUENCE: 33

| | |
|---|---|
| ngttgcacct attggccngc tggtctcgac tcctgacctc gttatctgcc tgcctcggcc | 60 |
| tcctaaagtg ctgggattac aggagtgagc cacagtgcct ggcctgtcaa gacttctctt | 120 |
| aagttaactt cctgagaagt gatgtctaaa agtatctttg ctggtgtgag aactccagtt | 180 |
| tccaacacat attatttccc tcaactattt ggaatatttt agaattttaa ttccaaagga | 240 |
| ttagtttgaa tacaagtatg ccacataact cagttttcgc catcttncat ttcttaacag | 300 |
| tgtaaattaa aagctaataa tcataataat aaagtgcatt taattatctt cgaaaaaaaa | 360 |
| aaancccttt tgggg | 375 |

<210> SEQ ID NO 34
<211> LENGTH: 809
<212> TYPE: DNA
<213> ORGANISM: Homo sapien
<220> FEATURE:
<221> NAME/KEY: misc_feature
<222> LOCATION: (1)...(809)
<223> OTHER INFORMATION: n = A,T,C or G

<400> SEQUENCE: 34

| | |
|---|---|
| ttgcacatgc tggccaggat ggtctcgatc tcctgacctc gtgatctgcc cgcctcggcc | 60 |
| tcccaaagtg ctggaactac aggtgtgagc caccacgcct ggcagctttg tgttctttc | 120 |
| tttctgtgat cttgccttag atcacacaga taaaacatga caggacctgg accttaacac | 180 |
| agtttggctc tcaatcctgt tctcataacc acnactgcct tcatttatct gtgtcatcct | 240 |
| cagacctgac acatagtagg tgctcagtca gtgttcacta agtaaatgat gaccaagaac | 300 |
| tctttgactg ggtccaaggt gcttatccca atacttcgcc atggctacct ccctcattcc | 360 |
| tcagctgact tgctctctct agcctggctg ctcctatttt atttcctaaa catgtgaccca | 420 |
| tggcaataag tttaaancta acangttgat acggtaccca tccataattt aatnaattnt | 480 |
| ggggctcatg caaccncaaa aaccagaacc caaaactacc tgtncncaaa caacaatcat | 540 |
| tttnggtngg gatcccntnc tngcttggnc cttttttta aaatgtccat tccccccgga | 600 |
| ctttaagaaa ttgaaggaat ncccggaaan tattgttanc gggccccctt nagngaaaaa | 660 |
| ggtggcnctc cnnncggggg ccctccctgt ccctgaaatt tnaaaacccc cctcccnntt | 720 |
| taaanccctt aatcccggnt aacancnaaa naaaattcta gggcccaaac ccanngggttt | 780 |
| ggttttaaaa aaccntntat ttttttnat | 809 |

<210> SEQ ID NO 35
<211> LENGTH: 192
<212> TYPE: DNA
<213> ORGANISM: Homo sapien

```
<220> FEATURE:
<221> NAME/KEY: misc_feature
<222> LOCATION: (1)...(192)
<223> OTHER INFORMATION: n = A,T,C or G

<400> SEQUENCE: 35
caccttattg ggatacagca gtgaattaag ctattaaaat aagataatga ttgcttttat      60
accttcagta gagaaaagtc tttgcatata aagtaatgtt taaaaaacat gtattgaaca     120
cgacattgta tgaagcacaa taaagattct gaagccaaaa aaaaaaaccc caangggggnt    180 nnttttnaaa aa                                                         192

<210> SEQ ID NO 36
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 36
ctgctagtac caantattat ttaagantac ttttcactac tcctaaataa tgacacagat      60
acgtttgtct tacacatttc actttattgt caagttatta gtatgtttat tttcaaaagt     120
tattttttgc aatttctttt tattattccg tacttttaa atttacttca ttatcacgtc     180
ttcctttatt cttttttaaat agtttttgct tttgttattt tgttttccct tttttactct    240
tggtttgtaa tacctctttc cttatttgct cctttctcat ttgatctcaa tgttaatcca    300
actgttttcc acatctgatt cactaaaatt ttagcccaaa aaaaaaancc cntttnggggg   360 gngntttt                                                              368

<210> SEQ ID NO 37
<211> LENGTH: 219
<212> TYPE: DNA
<213> ORGANISM: Homo sapien
<220> FEATURE:
<221> NAME/KEY: misc_feature
<222> LOCATION: (1)...(219)
<223> OTHER INFORMATION: n = A,T,C or G

<400> SEQUENCE: 37
ggccccattt cactctccat antggcnctt nctngaacag gcgtnctgga tnagtgcaca      60
tacnatccca tcnacntgca cctatancnc ttccactacg cacatcacca aanctgtgaa    120 aggggggcntn tcnttagaca cacaattgca gaatngacnn cncanccccgg gggannctcn   180 ngttcaccn tgnagcaggn gctggctcan gctnttata                             219

<210> SEQ ID NO 38
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 38
tcgatacagg gncagatctg ggagccaggg cgttgctgat gagttgcaca gacgatcaca      60
tctgaaacca ccagtaccac caccactacg cacatcacca aagcgctggc tcngcaatt     120 aangaggcca aagagcanca ccctgacatg tcngtgaccn ttgtantggt ccntaangac    180
```

| | |
|---|---|
| acngacatcg cctccaca | 198 |

<210> SEQ ID NO 39
<211> LENGTH: 560
<212> TYPE: DNA
<213> ORGANISM: Homo sapien
<220> FEATURE:
<221> NAME/KEY: misc_feature
<222> LOCATION: (1)...(560)
<223> OTHER INFORMATION: n = A,T,C or G

<400> SEQUENCE: 39

| | |
|---|---|
| tttnnatcng nacagctagt cctntaaant aatgacttca tagaaatggc attataattt | 60 |
| ttaagttgat actctacagg tagctattga tataattagt tttaataaaa catgctgcaa | 120 |
| ccatggtata caacaaaaat acatttcttt ggtgattgaa attaaggccg tatttacaat | 180 |
| gacttaatat aagactgact tttatcctgc ttcataactt gtatggagaa ctcaccaaga | 240 |
| aagaattcaa tactgtgaaa tatgcagcaa gaagattggt ctttacctag gctgtgtttc | 300 |
| ctaagctctg agttttcagc accagtagat ttgtattaaa agaaaaaaaa atggggcctt | 360 |
| agcttctggc ttttaatttt gccagctaag gacataaaac aaaantaanc aancaaaanc | 420 |
| aaatagccat ntgctatcag catcattatg taaaagaaaa tntattttag cccctaaaat | 480 |
| taggaagaat gtaatctcag aataaaggtt gtcatttaag ttgaataaat atntagcttt | 540 |
| cgaaaaaaaa aanccccttt | 560 |

<210> SEQ ID NO 40
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 40

| | |
|---|---|
| atacagggca gcgtgttagg tgaccacacc aggagcctca gcctcggtcc ttctcagccg | 60 |
| tcgggataag atccaggcat gncttttaaa tctcagaggt agcagtaaac ttttcantnt | 120 |
| tgcngttagc aagtgtgtgt ttgccaataa anccccatta tactaatgtg cctanttaat | 180 |
| gttcagggaa natctgcttc cactgtgtnc cnagggggtgn catgaactnt gtgagnagcc | 240 |
| ccncnnctgg agggatgaat gctgngttaa ctacngctat cacggatngt gtgntgtgaa | 300 |
| naatacatcn acatnaatnt tanntgctct gnaanttccc ttnttatntg tcaagtaact | 360 |
| ntttgtaaaa ntnntnctcc caanttatta cngtgattac taatnnattn gtnccatgtt | 420 |
| t | 421 |

<210> SEQ ID NO 41
<211> LENGTH: 411
<212> TYPE: DNA
<213> ORGANISM: Homo sapien
<220> FEATURE:
<221> NAME/KEY: misc_feature
<222> LOCATION: (1)...(411)
<223> OTHER INFORMATION: n = A,T,C or G

<400> SEQUENCE: 41

| | |
|---|---|
| aggtagaggt tgtgcatgtt gtcctttta tctgatctgt gattaaagca gtaatatttt | 60 |
| aagatggact gggaaaaaca tcaactcctg aagttagaaa taagaatggt ttgtaaaatc | 120 |
| cacagctata tcctgatgct ggatggtatt aatcttgtgt agtcttcaac tggttagtgt | 180 |

```
gaaatagttc tgccacctct gacgcaccac tgccaatgct gtacgtactg catttgcccc    240
ttgagccagg tggatgttta ccgtgtgtta tataacttcc tggctccttc actgaacatg    300
cctantccaa cattttttcc cagtggagtc ncatcctggg atccagtgta taaatcccaa    360
ttatcatgtc ttgtgcataa attcttccca aaagggatct ntaatttttt g             411
```

<210> SEQ ID NO 42
<211> LENGTH: 408
<212> TYPE: DNA
<213> ORGANISM: Homo sapien
<220> FEATURE:
<221> NAME/KEY: misc_feature
<222> LOCATION: (1)...(408)
<223> OTHER INFORMATION: n = A,T,C or G

<400> SEQUENCE: 42

```
ggctcccctc cctaactctc taagtacttc ccttacccac tcagtgtggt gatggcacct    60
ccctgaatct cctgacaaat gcgaacagga actcctattc atcaggagcc aacttgataa    120
ctganaagat tcctctctca tttatcagcc tttgattatc tttttgtgtc tcttactatt    180
tgcgcttagc gagaaaaata aagaggtttg aacaattaag aagtaacaaa gagctcatag    240
ttcacaaaga gcaantcaaa ggatgtctgg aatatttgaa catacaactg cctttggcat    300
gaggtggcct acatacattc tcaggggcag gataggctgg nanagctgat caagctgccg    360
ggaaagctga agcaaaggca gggttgggtg gaaatcaaaa tntctctt                408
```

<210> SEQ ID NO 43
<211> LENGTH: 275
<212> TYPE: DNA
<213> ORGANISM: Homo sapien
<220> FEATURE:
<221> NAME/KEY: misc_feature
<222> LOCATION: (1)...(275)
<223> OTHER INFORMATION: n = A,T,C or G

<400> SEQUENCE: 43

```
tccctaactc tctaagtact tcccttaccc actcagtgtg gtgatggcac ctccctgaat    60
ctcctgacaa atgcgaacag gaactcctat tcatcagagc caacttgata actgagaaga    120
ttcctctctc atttatcagc ctttgattat cttttgtgt ctcttactat ttgcgcttag    180
caagaaaaat aaagaggttt gaacaantaa gaagtancnn ggagctcnta gttcanaagn    240
agcaagtcaa aggatgtctg gangatttga agggt                               275
```

<210> SEQ ID NO 44
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 44

```
tttggtccca agcacatttc acaaangaga atttacacct agcacagctg gtgccangan    60
atntcctang gacatggcca cctgggtcca ctccagcgac agaccctga caagagcagg    120 tctctggagg ctnantngca tggggcctan tntcntcaat cnaatgagcc ccnantgcta    180
ctgcgccccg ggggctccca cggcctgggc nnctttcntg caactgnaaa aggatagngg    240
tatttc                                                               246
```

<210> SEQ ID NO 45
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 45

| | | | | | |
|---|---|---|---|---|---|
| tttggctccg | tgggacgttg | tantgtgcnc | agacatttcc | aagggaaatt | ctaaacagtc | 60 |
| accctnccct | tttgcattcc | cccaaatctt | aagtgtatac | ataaaaccct | gggtacatat | 120 |
| tgtngtggta | atagaaggga | attggnnaaa | cngtacactt | gttatatgga | antnactgtg | 180 |
| gccacctaca | aaagacaagt | taacaaactg | tcntggaggc | tgtngntgcc | canccagggc | 240 |
| cgctgcnttt | tgacaacatt | cccaccctgg | ccactcagca | canttcatgg | caggtcatgt | 300 |
| ctntncactg | anacntttnt | ganactttt | catatagcan | aatcc | | 345 |

<210> SEQ ID NO 46
<211> LENGTH: 969
<212> TYPE: DNA
<213> ORGANISM: Homo sapien
<220> FEATURE:
<221> NAME/KEY: misc_feature
<222> LOCATION: (1)...(969)
<223> OTHER INFORMATION: n = A,T,C or G

<400> SEQUENCE: 46

| | | | | | |
|---|---|---|---|---|---|
| aattgcagtt | ctttcttgcc | tttaacaaca | ttagggcctt | tagaatgagt | acctggtgct | 60 |
| gtccttccaa | ctctgtgatt | ctctgattcc | atcctcattt | ttcaccatca | ctggtgtact | 120 |
| ggcaagaacc | antatgagat | ttgaggaaaa | atacttggat | tactctttt | taaaaaaaat | 180 |
| tatttagata | taattcccat | accatacaat | taacctttt | atgtgtataa | ttcagtattt | 240 |
| ntagtatatc | cacaaagttg | tgctaccatc | accactatcc | gattccagag | cttgtcatca | 300 |
| tacaaaaaaa | aaaacccan | agtnanttcc | tttcaaaacn | ctttnngttn | ttcnttntnc | 360 |
| ccntgtngcn | tctagnncg | ngggntnnct | tttgtcnntn | tcnccctncn | ctcatcntnn | 420 |
| cnggtctctg | ctcngngnnn | cgntntgnct | tnnantcgct | gctnntcntg | tattcccgc | 480 |
| nctngtnnng | tctgcnncgt | agccagtggn | cctcctgntn | ccnncgntt | ctntntncgg | 540 |
| cacannntcca | nccanctgcc | atnagtnana | nnatctctnt | tcnncanctg | ntnncagnnt | 600 |
| tgtcntcntc | tccgtnccnc | cngcngctnn | ctcnttncgc | nctggnngnc | antcgtacct | 660 |
| ggcttttatc | cccctntccn | nctnttctng | atggnntctc | ntctcnacac | ctgncgttac | 720 |
| gnntctcntn | tnncnnnann | cgttnctntn | tnncttnccg | ncngccatct | nagctcannc | 780 |
| tggngcgant | cncgctctgn | gtatcagtca | tntanagann | ngngnntgtt | nccnncgcgn | 840 |
| nntgagannc | ccncccnctt | cgcatnacgt | angtgnctt | ntnnatctgc | tcgtcgtctc | 900 |
| nctcatatcc | nccatgctgn | catganactc | cntantctnn | cgcnnttctn | ncgttccctc | 960 |
| tgcccttnn | | | | | | 969 |

<210> SEQ ID NO 47
<211> LENGTH: 361
<212> TYPE: DNA
<213> ORGANISM: Homo sapien
<220> FEATURE:
<221> NAME/KEY: misc_feature
<222> LOCATION: (1)...(361)
<223> OTHER INFORMATION: n = A,T,C or G

<400> SEQUENCE: 47

```
ggccactaag caggtcttac cnaatttaag aanattgaan tcctatcaag tatctcttct      60
gaccacaatg gtatgaaact agaaatcagt aacaggagga aaattggaag attcacaaat     120
ntgtggaant taatcaacnc atgagcaact antgagtcna agancanatc aaaagggann     180
tcaaaaactc tcttgaggtg gatgagaatg ganatacaac ataccngaac tcatgggatg     240
tatcacaagc ngtgctaagg gggaagttta agtnctagat gtctanatta ngaaagggaa     300
agatctcana tanacnaccc agcnttncnc ctcgaanaac tagaaaaact aagaaaaaac     360
t                                                                    361
```

<210> SEQ ID NO 48
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 48

```
atgatgacca catntagatg gcacatngat gaggacttta atctttcctt aaanacaata      60
atgtgttctt ttttctttta ntcacatgat ttctaagtan attttncatg caggacactt     120
tttcaaccct tgatgtacant gactgtgtaa aatttntctt tcagtggcaa cctctataat     180
ctttannata tggtgagcat ctngtctgtt tagaanggga tatgacaata aatctatcag     240
atggaaaatc ctgttacaaa gtataaaagc tttagtaatt tactcagtgt ggtggtttta     300
tccttttttgc tttttctccc ttggtctata atgaaattgt tacagcagtg caaaataaaa     360
tcct                                                                 364
```

<210> SEQ ID NO 49
<211> LENGTH: 703
<212> TYPE: DNA
<213> ORGANISM: Homo sapien
<220> FEATURE:
<221> NAME/KEY: misc_feature
<222> LOCATION: (1)...(703)
<223> OTHER INFORMATION: n = A,T,C or G

<400> SEQUENCE: 49

```
atggggaatc aaacaatgtt aaaaggctan taatacttat aggttttatg attcaattta      60
ctatgtgttt aaaattgttt tttgaaaaaa ttgagttatg tcnctaaaac tgagtctnta     120
cagctcaaaa atgaagaaat acntatctcc gataagcata ttatgtgaat ttcaacatcn     180
ctattgagaa aaggaatata aatttgaatg aaaatgaaac tctatctttc tatatcacat     240
tgcataggtg taggctagtg agtactttga tgtaaattgc tgtatctttt gaggcntcna     300
tttggcnata tagatcagaa ttttaaatcn gcatactttg tttgccagaa atctatcagg     360
accacttgta ntnattttgt tnaaaggaat atcnaacnct tggatgttca ncncagtatt     420
gattgtttta naagaaggaa anggagaaag ggaggagaat ggaaganana aaggaggga     480
ggaanattgg aaccnttgac atntgtgata gcatnggatt tgctnaacac nctatantat     540
accccctngca tgggananagc atgcacnctn aaacaaggac nngttngatg gntctacnnt     600
ttgacntcag atnnaantaa atnaaaaaaa aaancccccn cctctttgnn ttcctntcnn     660
cgnnnnannc ntctccccnc nncgnccnnc nccgccacc ntn                       703
```

<210> SEQ ID NO 50
<211> LENGTH: 413
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 50

| | | | | | | |
|---|---|---|---|---|---|---|
| tcttggctgg | ttgagtattc | aanaatcagg | cacggagaag | tggggtggat | gcaaaccaac | 60 |
| tgaccactgt | ggcaccacca | gcagtttcag | ttttcatctt | gantgtcnag | aggaaatatc | 120 |
| taatcttaca | actcnttagg | ggcctggctc | agtggctcat | accttgtntt | cccancactt | 180 |
| tgggangccg | angcnggcnt | atcacccgca | ngtcaggatt | ttgagaccac | cctggccaac | 240 |
| ntggtgaaac | cccatctcta | ctantcaata | caaancttag | ctangcgtga | tggcatgcac | 300 |
| ctctaatccc | acttacttgg | gangctgagg | cagcganaat | cacttgtaac | ccggaaggca | 360 |
| nacgttgcat | ntgagccaag | atcgtgccac | tgcactccat | cctgggcttt | cta | 413 |

<210> SEQ ID NO 51
<211> LENGTH: 252
<212> TYPE: DNA
<213> ORGANISM: Homo sapien
<220> FEATURE:
<221> NAME/KEY: misc_feature
<222> LOCATION: (1)...(252)
<223> OTHER INFORMATION: n = A,T,C or G

<400> SEQUENCE: 51

| | | | | | | |
|---|---|---|---|---|---|---|
| gttacagaca | aggnttntag | aatatcttat | gttttatgct | ctgtaagttc | aaagaagnta | 60 |
| gcagaaaaca | taagcatact | gaaaagagaa | acagaagcta | tttttttaaat | acctatgtga | 120 |
| aatctctcta | tntgaaacaa | aaaatacact | ggatggatta | gacactgcag | aaggaaaatt | 180 |
| tggtgaactt | gagatcttat | aaataaaaat | tatccaaaat | gaagtgtaga | gtgaaaaaaa | 240 |
| aaaanccccct | at | | | | | 252 |

<210> SEQ ID NO 52
<211> LENGTH: 875
<212> TYPE: DNA
<213> ORGANISM: Homo sapien
<220> FEATURE:
<221> NAME/KEY: misc_feature
<222> LOCATION: (1)...(875)
<223> OTHER INFORMATION: n = A,T,C or G

<400> SEQUENCE: 52

| | | | | | | |
|---|---|---|---|---|---|---|
| agaaacgaga | atgganattc | aaatacgtcn | gccgggcttg | gtggattaga | cctgtaaccc | 60 |
| naacactttg | ggaggnctag | gtgggcggat | caccngaggt | cnngagtacg | ggaacanccct | 120 |
| ggcaaaaacc | ccntctttan | tctgngaaaa | cncaactcta | ctaaaanaac | tactcttaga | 180 |
| tnggcgtngn | tgcgcctgcc | tgttntccca | gatacnnttt | naggctgang | tggggataan | 240 |
| tnctttaaca | tgggaagtgg | aagttgcact | gatccaatgt | ctccacactg | cantccagcc | 300 |
| tgggttangg | aatgagaccc | cncncacgga | aaggacaata | aaaancccccn | nnggnnttnn | 360 |
| tttttaangg | cctcttgntc | nttttcttnt | antgcncgcc | tncgcnnncn | ttgntntgtc | 420 |
| gantcnnntg | cnnttntttc | ttcnncctcn | ancctgcttc | tnntcnnttc | gccnntnnac | 480 |
| ngcttccccc | ntncctagc | acttnnnttc | tntcgntccn | nnatctccnn | cttntctnnn | 540 |
| ccgctcgcgt | nnnccntnan | ctcgnntcnt | nccctttctt | cncngcnncn | ntttcgncna | 600 |

```
gatcgtncgn ctctatctac ttctntccnn gntntanata tngatnttac attntgctcn    660
atnacccatn annncntcta tgtttatann ngtnnnnccn ttcaacnnnn cnttatgagn    720
tcttnactca gctctncgtt gntnttccna ctanngttgn ncntncatgt nctgtcncgt    780
ancnctctnc tcntcncngt cntgagacna atctctatnt atngnttatn cctgcntnct    840
ganctncacc gngatctcgg cnntntcttc tcaag                              875
```

<210> SEQ ID NO 53
<211> LENGTH: 182
<212> TYPE: DNA
<213> ORGANISM: Homo sapien

<400> SEQUENCE: 53

```
ccagaagaag ggctacatat ggactcatgt tgggcctact cctgcaataa caattaagga     60
atcagttgcc aaccatttgt agttcacaaa ttaaaactgg gtttccaggc ctggtgtggt    120
ggctcacgcc tgtagcccca gctattgcac cactgctctc caagctgggc aatggagtca    180
ga                                                                   182
```

<210> SEQ ID NO 54
<211> LENGTH: 329
<212> TYPE: DNA
<213> ORGANISM: Homo sapien

<400> SEQUENCE: 54

```
catgatgcga gactggacat ctctcctacc ccatgtacac ttcagctgag caggcagaat     60
tagagagtca ggactagaag ttcagtctag ggatcaaata ataatagtag ctaatgttta    120
aaggtaccta agatccgcca ggagacatac tcagtatagt tccgtggttt gccacatttc    180
atcttatcca gtagcacagg tgaaatttgt cttatgtgta tactgaggaa aaacaagtcc    240
ctctgatacc agcagccaat aaatgacaaa gctgggatag aaacttactt cattctaacc    300
cgagagtccc tgttcttgca tggggcaca                                      329
```

<210> SEQ ID NO 55
<211> LENGTH: 312
<212> TYPE: DNA
<213> ORGANISM: Homo sapien
<220> FEATURE:
<221> NAME/KEY: misc_feature
<222> LOCATION: (1)...(312)
<223> OTHER INFORMATION: n = A,T,C or G

<400> SEQUENCE: 55

```
actcaactcg tttgagctat aggaatnggc cattcgnngt ggctcanacc tgtaatccca     60
gnatttnggg anacctcact aggatcacnt gaggtcagga gttcaagacc agcctgtcca    120
acatggngaa accccatctc tantanaaaa tacagaaatt atccaggtgt ggtggctggc    180
acctgtaatc ccagctactt gggaggccaa ggcatggaaa attgtctgaa cctgggaagt    240
ggaggttgcg gtnanctgan atcatgccat tgctctccag cctcggccac anatcaagac    300
cctatctcaa aa                                                        312
```

<210> SEQ ID NO 56
<211> LENGTH: 565
<212> TYPE: DNA
<213> ORGANISM: Homo sapien

<400> SEQUENCE: 56

| | |
|---|---|
| acaatttcac acaggaaaca gctatgacat gattacgaat ttaatacgac tcactatagg | 60 |
| gaatttggcc ctcgaggcca agaattcggc acgagggat ccaacgtcgc tccagctgct | 120 |
| cttgacgact ccacagatac cccgaagcca tggcaagcaa gggcttgcag gacctgaagc | 180 |
| aacaggtgga ggggaccgcc caggaagccg tgtcagcggc cggagcggca gctcagcaag | 240 |
| tggtggacca ggccacagag gcggggcaga aagccatgga ccagctggcc aagaccaccc | 300 |
| aggaaaccat cgacaagact gctaaccagg cctctgacac cttctctggg attgggaaaa | 360 |
| aattcggcct cctgaaatga cagcaggag acttgggtcg gcctcctgaa atgacagcag | 420 |
| ggagacttgg gtgacccccc ttccaggcgc catttagcac agcctggccc tgatctccgg | 480 |
| gcagccacca cctcctcggt ctgccccctc attaaaattc acgttcccaa aaaaaaaaa | 540 |
| aaaaaaaaag atgcggccgc aagct | 565 |

<210> SEQ ID NO 57
<211> LENGTH: 798
<212> TYPE: DNA
<213> ORGANISM: Homo sapien

<400> SEQUENCE: 57

| | |
|---|---|
| ggaacaagta gaagggaaga gggaaatgga gagcatcctt atgactttac aaagggtgga | 60 |
| aatgaggatg gagggataca gaagtctgca cagctgtaaa ggttttatag atgtctttgc | 120 |
| cttcccttct gaggaaggga agaagtaatg aaagcacatg tgaataaccc cttccatccc | 180 |
| attcacagca tcgcactccc agtccttaag gcaaaggag gcagtgctga agcattggtg | 240 |
| gtgcagtgta aagagacaag acctgatcat ctgatcacac ttgtgccaac ttgattcata | 300 |
| ttgggcatta ctaacaaccc ctggtcaagg taaataggtt gaacaatcaa taacattatc | 360 |
| cctgcctgca tacatgtgaa caaaagctat agaggacatg caaattctac agtcattcct | 420 |
| catatgcttt agacagagtg cagctactgg aatcttccag atttcagtgt tttaaaatca | 480 |
| gagctctgaa tacacaaaag gaaagagaaa tggagcagct gacatatttt aagctcacag | 540 |
| tgatactcag tgcaggagc acagagctct aatgtccaca ggatgttgta gggtagggtc | 600 |
| tctcagtaaa tcaagtccct tacctatgtt ctgacactga ggctcttgga gctatgggtt | 660 |
| agaaatccag gaggcaatat gtctttattc taatgaagtc ctcatcttgc actcagaggc | 720 |
| ccactagttt gcccttctat atattaagta aaaccaagag aaattaaaaa aaaaaaagcc | 780 |
| ctatagtgag tcgtatta | 798 |

<210> SEQ ID NO 58
<211> LENGTH: 729
<212> TYPE: DNA
<213> ORGANISM: Homo sapien

<400> SEQUENCE: 58

| | |
|---|---|
| aagaatagac cgagataggg ttgagtgttg ttccagtttg gaacaagagt ccactattaa | 60 |
| agaacgtgga ctccaacgtc aaagggcgaa aaaccgtcta tcagggcgat ggcccactac | 120 |
| gtgaaccatc accctaatca gttttttgg ggtcgaggtg ccgtaaagca ctaaatcgga | 180 |
| accctaaagg gagcccccga tttagagctt gacggggaaa gccggcgaac gtggcgagaa | 240 |
| aggaagggaa gaaagcgaaa ggagcgggcg ctagggcgct ggcaagtgta gcggtcacgc | 300 |
| tgcgcgtaac caccacaccc gccgcgctta atgcgccgct acaggcgcg tccattcgcc | 360 |
| attcaggctg cgcaactgtt gggaagggcg atcggtgcgg gcctcttcgc tattacgcca | 420 |
| gctggcgaaa gggggatgtg ctgcaaggcg attaagttgg gtaacgccag ggttttccca | 480 |

```
gtcacgacgt tgtaaaacga cggccagtga attgtaatac gactcactat agggcgaatt      540
gggccctcta gatgcatgct cgagcggccg ccagtgtgat ggatatctgc agaattcggc      600
ttgtaatacg actcactata gggctttttt tttttcggt ttgaggggga atgctggaga       660
ttgtaatggg tatggagaca tatcatataa gtaatgctag tcttatcctg tgtgaaattg     720
ttatccgct                                                              729

<210> SEQ ID NO 59
<211> LENGTH: 730
<212> TYPE: DNA
<213> ORGANISM: Homo sapien

<400> SEQUENCE: 59
aagaatagac cgagataggg ttgagtgttg ttccagtttg gaacaagagt ccactattaa       60
agaacgtgga ctccaacgtc aaagggcgaa aaaccgtcta tcagggcgat ggcccactac     120
gtgaaccatc accctaatca agttttttgg ggtcgaggtg ccgtaaagca ctaaatcgga     180
accctaaagg gagcccccga tttagagctt gacggggaaa gccggcgaac gtggcgagaa     240
aggaagggaa gaaagcgaaa ggagcgggcg ctagggcgct ggcaagtgta gcggtcacgc     300
tgcgcgtaac caccacaccc gccgcgctta atgcgccgct acagggcgcg tccattcgcc     360
attcaggctg cgcaactgtt gggaagggcg atcggtgcgg gcctcttcgc tattacgcca     420
gctggcgaaa gggggatgtg ctgcaaggcg attaagttgg gtaacgccag ggttttccca     480
gtcacgacgt tgtaaaacga cggccagtga attgtaatac gactcactat agggcgaatt     540
gggccctcta gatgcatgct cgagcggccg ccagtgtgat ggatatctgc agaattcggc     600
ttgtaatacg actcactata gggctttttt tttttcggt ttgaggggga atgctggaga      660
ttgtaatggg tatggagaca tatcatataa gtaatgctag tcttatcctg tgtgaaattg     720
ttatccgcta                                                             730

<210> SEQ ID NO 60
<211> LENGTH: 623
<212> TYPE: DNA
<213> ORGANISM: Homo sapien

<400> SEQUENCE: 60
gactccaaga gaagactagg aagtagccct cgttctccag ggcacccaaa ataccagcct       60
ttattgtctg catgatttta ggggatatgg ggagggaaca agtagaaggg aagagggaaa     120
tggagagcat ccttatgact ttacaaaggg tggaaatgag gatggaggga tacagaagtc     180
tgcacagctg taaaggtttt atagatgtct ttgccttccc ttctgaggaa gggaagaagt     240
aatgaaagca catgtgaata accccttcca tcccattcac agcatcgcac tcccagtcct     300
taaggcaaag ggaggcagtg ctgaagcatt ggtggtgcag tgtaaagaga caagacctga     360
tcatctgatc acacttgtgc caacttgatt catattgggc attactaaca accctgggc     420 aagtaaaata ggttgaacaa tcaataacat tatccctgcc tgcatacatg tgaacaaaag     480
ctatagagga catgcaaatt ctacagtcat tcctcatatg ctttagacag agtgcagcta     540
ctggaatctt ccagatttca gtgctttaaa atcagagctc tgaatacaca aaaaaaaaa     600 gccctatagt gagtcgtatt aca                                              623

<210> SEQ ID NO 61
<211> LENGTH: 376
<212> TYPE: DNA
```

<213> ORGANISM: Homo sapien

<400> SEQUENCE: 61

| | | | | | |
|---|---|---|---|---|---|
| gcatgctcga | gcggccgcca | gtgtgatgga | tatctgcaga | attcggctta | gcggataaca | 60 |
| atttcacaca | ggatccatga | ctcagctatt | aaggctctgg | ccttggatcc | ctatgaggaa | 120 |
| tattttacca | caggttcagc | agaaggtaac | ataaaggttt | ggagattgac | aggccatggc | 180 |
| ctaattcatt | catttaaaag | tgaacatgct | aagcagtcca | tatttcgaaa | cattggggct | 240 |
| ggagtcatgc | agattgacat | catccagggc | aatcggctct | tctcctgtgg | tgcagatggc | 300 |
| acgctgaaaa | ccagggtttt | gcccaatgct | tttaacatcc | taacagaat | tcttgacatt | 360 |
| ctataaagat | tggggt | | | | | 376 |

<210> SEQ ID NO 62
<211> LENGTH: 539
<212> TYPE: DNA
<213> ORGANISM: Homo sapien

<400> SEQUENCE: 62

| | | | | | |
|---|---|---|---|---|---|
| atgactcatt | gtttctctgc | ctttccgtgt | gttacaggtg | ggctgatccc | cctgcagcca | 60 |
| gtttcccata | agcaactgac | ttccaactgg | gaatgtctcg | ggggataatg | ggggtgggga | 120 |
| tatggaagta | tagagaaaac | ataagaaaat | actgggtgta | tacactttc | tctctctgag | 180 |
| tatgatgaca | atgtgatagt | cagtgtggca | tctgcgactc | cagcttgtgc | ctggcatgta | 240 |
| caccctagct | ccagcttccc | ctgggagact | gtgcatctcc | tggctccact | aacaccacct | 300 |
| tcttctgacc | ttccagccta | gagatgatga | ctctgccagc | ctagatgggc | tctgggttgt | 360 |
| ctccctattc | ctgtttgctt | tgtagatttc | ccattatgct | gtcaccaact | ccccagccta | 420 |
| agccctctct | attttaaatt | ctcaagtgga | ttatgttcct | gattagtccc | tgactgatat | 480 |
| accactctcc | tcatgatctc | tgattagttt | tcctgttagg | ttgttgcagt | aaaaaaaaa | 539 |

<210> SEQ ID NO 63
<211> LENGTH: 304
<212> TYPE: DNA
<213> ORGANISM: Homo sapien

<400> SEQUENCE: 63

| | | | | | |
|---|---|---|---|---|---|
| ggcttagcgg | ataacaattt | cacacaggac | gactccaagc | tgggaaggaa | aattcccttt | 60 |
| tccaacctgt | atcaattttt | acaacttttt | tcctgaaagc | agtttagtcc | atactttgca | 120 |
| ctgacatact | ttttccttct | gtgctaaggt | aaggtatcca | ccctcgatgc | aatccaccttt | 180 |
| gtgttttctt | agggtggaat | gtgatgttca | gcagcaaact | tgcaacagac | tggccttctg | 240 |
| tttgttactt | tcaaaaggcc | cacatgatac | aattagagaa | ttcccaccgc | acaaaaaaaa | 300 |
| aaag | | | | | | 304 |

<210> SEQ ID NO 64
<211> LENGTH: 226
<212> TYPE: DNA
<213> ORGANISM: Homo sapien
<220> FEATURE:
<221> NAME/KEY: misc_feature
<222> LOCATION: (1)...(226)
<223> OTHER INFORMATION: n = A,T,C or G

<400> SEQUENCE: 64

| | | | | | |
|---|---|---|---|---|---|
| atgatgatga | ccatgtggac | agccaggact | ccattgactc | gaacgactct | gatgatgtng | 60 |
| atgacactga | tgattctcac | cagtctgatg | agtctcacca | ttctgatgaa | tctgatgaac | 120 |

```
tggtcactga ttttcccncg gacctgccng caaccgaagt nttcactcca gttgtccccc    180
cagtagacac ntntgatggc cgaggtgatg gtgtggttta tggact                  226
```

<210> SEQ ID NO 65
<211> LENGTH: 225
<212> TYPE: DNA
<213> ORGANISM: Homo sapien
<220> FEATURE:
<221> NAME/KEY: misc_feature
<222> LOCATION: (1)...(225)
<223> OTHER INFORMATION: n = A,T,C or G

<400> SEQUENCE: 65

```
taccaacaga gcttctgaaa cagataccat agcattggag agaaaaacag ctcacagtct    60
gaggaagatg atattganag aaggaaagaa ttgaaagcat cttgaagaaa aactcagatt   120
ggatntggga ttggtcaagt cggccggata atattccccc caaggagttc ctcttaaaac   180
acccgaagcg cacggccacc ctcagcatga ggaacacgag cgtca                   225
```

<210> SEQ ID NO 66
<211> LENGTH: 240
<212> TYPE: DNA
<213> ORGANISM: Homo sapien
<220> FEATURE:
<221> NAME/KEY: misc_feature
<222> LOCATION: (1)...(240)
<223> OTHER INFORMATION: n = A,T,C or G

<400> SEQUENCE: 66

```
ccagcatggt ggccgtnatg gatagcgacc cacangcaag ctgggctttg aggaattcaa    60
gtacttgtgg aacaacatca aaaggtggca ggccatatac aaacagtacg acactgaccg   120
atcagggacc atgtgcagta gtgaactccc angtgccttt gaggcagcan ggttccacct   180
gaatgaacan ctctataaca tgatcatccg acnctactca gatgaaagtg ggaacatgga   240
```

<210> SEQ ID NO 67
<211> LENGTH: 504
<212> TYPE: DNA
<213> ORGANISM: Homo sapien
<220> FEATURE:
<221> NAME/KEY: misc_feature
<222> LOCATION: (1)...(504)
<223> OTHER INFORMATION: n = A,T,C or G

<400> SEQUENCE: 67

```
cacgaggaga gatngcatct gctatatatt ccacngatac atgtgagtna ctgatagaaa    60
aaatcgcnnc ggngaacact gncaccggtn ccggcccccg gtactacagg gatctcntca   120
gacttcaccg tntactacaa ngtaagcncc ctttaagaat gtcacggagt atgatgggca   180
ggatgcctgc ggctccaaca nctggaacnt ggtggacgtg gacctcccgc caacaagga    240 cntggagccc ggcatcttac tacatgggct gaanccctgg actcagtacg ccgtttacnt   300
caaggctgtg accctcacca tggtggagaa cgaccatatc cgtggggcca agagtgagat   360
cttgtncatt cgcnccantg cttcngttcc ttccnttccc ttggacnttc tttcggcatc   420
aaactcctct tctcagttaa tcgtgaagtg gaaccctccc tctctgccca acggcnacct   480
gagttactac tttgtgcnct ggca                                          504
```

<210> SEQ ID NO 68
<211> LENGTH: 462
<212> TYPE: DNA

<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 68

| | | | | | |
|---|---|---|---|---|---|
| tggatggcag | ggggagaaag | gaaaagcaaa | acactccagg | acctctcccg | gatctgtctc | 60 |
| ctcctctagc | cagcagtatg | gacagctgga | ccctgaact | tcctctcctc | ttacctgggc | 120 |
| agagtgttgt | ctctccccaa | atttataaaa | actaaaatgc | atnccattcc | tctgaaagca | 180 |
| aaacaaattc | ataattgagt | gatattaaat | anagaggttt | tcggaagcag | atctgtgaat | 240 |
| atgaaataca | tgtgcatatt | tcattcccca | ggcagacatt | ttttagaaat | caatacatgc | 300 |
| cccaatattg | gaaagacttg | ttcttccacg | gtgactacag | tacatgctga | agcgtgccgt | 360 |
| ttcagccctc | atttaattca | atttgtaagt | agcgcagcag | cctctgtggg | ggaggatagg | 420 |
| ctgaaaaaaa | aaaancccct | tttttngtnt | nttttaaaaa | aa | | 462 |

<210> SEQ ID NO 69
<211> LENGTH: 357
<212> TYPE: DNA
<213> ORGANISM: Homo sapien

<400> SEQUENCE: 69

| | | | | | | |
|---|---|---|---|---|---|---|
| agaagtcttc | ctgagccttc | catgtatcct | cggtgcccgg | ggattaacca | gcgttatcaa | 60 |
| ccaaagctaa | aggatgatga | ggttgctcag | ctcaagaaaa | gtggagatac | cctgtgggac | 120 |
| atccagaagg | acctaaaaga | cctgtgacta | gtgagctcta | ggctgtagaa | atttaaaaac | 180 |
| tacaatgtat | taactcgatc | ctttagtttt | catccatgta | catggatcac | agtttgcttt | 240 |
| gatcttcttc | aattgtgaat | ttgggctcac | agaatcaaag | cctatgcttg | gtttaatgct | 300 |
| tgcaatctga | gctcttgaac | aaataaaatt | aactattgta | gtgtgaaaaa | aaaaaaa | 357 |

<210> SEQ ID NO 70
<211> LENGTH: 226
<212> TYPE: DNA
<213> ORGANISM: Homo sapien
<220> FEATURE:
<221> NAME/KEY: misc_feature
<222> LOCATION: (1)...(226)
<223> OTHER INFORMATION: n = A,T,C or G

<400> SEQUENCE: 70

| | | | | | |
|---|---|---|---|---|---|
| atgatgatga | ccatgtggac | agccaggact | ccattgactc | gaacgactct | gatgatgtng | 60 |
| atgacactga | tgattctcac | cagtctgatg | agtctcacca | ttctgatgaa | tctgatgaac | 120 |
| tggtcactga | ttttcccncg | gacctgccng | caaccgaagt | nttcactcca | gttgtccccc | 180 |
| cagtagacac | ntntgatggc | cgaggtgatg | gtgtggttta | tggact | | 226 |

<210> SEQ ID NO 71
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 71

| | | | | | |
|---|---|---|---|---|---|
| agcagacaag | ccacaattaa | cataggggtac | aattgggtca | tgtagctcat | gggaaatcca | 60 |
| cagtcgtcaa | agctatttct | ggagttcata | ctgtcaggtt | caaaaatgaa | ctagaaagaa | 120 |

```
atattacaat caagcttgga tatgctaatg ctaagattta taagcttgat gacccaagtt        180
gccctcggcc agaatgttat agatcttgtg ggagcagtac acctgacgag tttcctacgg        240
acattccagg gaccaaaggg aacttcagat tagtcagaca tgtttccttt gttgactgtc        300
ctggccacna tattttgatg gctactatgc tgaacggtgc agcagtgatg gatgcagctc        360
ttctgttgat agctggtaat gaatcttgcc ctcagcctca gacatcggaa acacctggct        420
gctatagaag atcatgaaac tggaagccat attttgaatt ctacaaaata aaattga          477
```

<210> SEQ ID NO 72
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 72

```
ccaagccaga ttgtcactcc agctgatctt ctttgatggt gaagaggctt ttcttcactg         60
gtctcctcaa gattctctct atgggtctcg acacttaact gcaaagatgg catcgacccc        120
gcacccacct ggagcgagag gcaccagcca actgcatggc atggatttat tggtcttatt        180
ggatttgatt ggagctccaa acccaacgtt tcccaatttt tttccanact cagccaggtg        240
gttcgaanga cttcaagcan ttgaacatga acttcatgaa ttgggtttgc tcaangatca        300
ctctttggag gggcggtatt tccanaatta cagttatgga ggtgtgattc aggatgaccn        360
ttttccattt ccaa                                                         374
```

<210> SEQ ID NO 73
<211> LENGTH: 597
<212> TYPE: DNA
<213> ORGANISM: Homo sapien
<220> FEATURE:
<221> NAME/KEY: misc_feature
<222> LOCATION: (1)...(597)
<223> OTHER INFORMATION: n = A,T,C or G

<400> SEQUENCE: 73

```
ccaagggatc tgtaaagaat atatacttga gtggtgtgtg ttatcagata aagcaccctg         60
tatcacagac tggcaacaag aagatggtac cgtgcatcgc acctatttaa gagggaactt        120
agcagagagc aaatgctatt tgataacagt tactccagta tatgctgatg gaccaggaag        180
ccctgaatcc ataaaggcat accttaaaca agctccacct tccaaaggac ctactgttcg        240
gacaaaaaaa gtagggaaaa acgaagctgt cttanagtgg gaccaacttc ctgttgatgt        300
tcanaatgga tttatcagaa attatactat attttatana accatcattg gaaatgaaac        360
tgctgtgaat gtggattctt cccacacaga aatntacatt gtcctctttg actagtgaca        420
cattgtacat ggtacgaatg gcagcataca cagatgaagg tgggaaggat ggtccaaaat        480
tcacttttac tacccccaaan tttgctcaag gganaaattg aagccatant cgtgcctgtt        540
tgcttancat tcctattgac aactcttctg ggaatgctgt tctgctttaa taagcga          597
```

<210> SEQ ID NO 74
<211> LENGTH: 257
<212> TYPE: DNA
<213> ORGANISM: Homo sapien
<220> FEATURE:
<221> NAME/KEY: misc_feature
<222> LOCATION: (1)...(257)

<223> OTHER INFORMATION: n = A,T,C or G

<400> SEQUENCE: 74

| tggtaaaggg taatagccag agnntagaac cttgangaga tgcggccaan gattctttat | 60 |
| atctgaaccn agatgtnaaa naagaaaatg ctttgaggct ttctaagcga tcctcctgtc | 120 |
| taatttncac ctttgtctgg atgcacactt ctgaccncgc tgccacaacc tgtgggtct | 180 |
| gatgtgtccc ttgatgggtg cggccctcag ggactgcacc ctgacaagtg ttnaggcaan | 240 |
| attcctttct tgtgccc | 257 |

<210> SEQ ID NO 75
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 75

| tgttcataag gctggtgata nagggtctt gtcatggaaa ggtgctcttc caggaaacct | 60 |
| ctgtgtatgg aggtcgnagc cacaatacgc ggacgangat gtgaacacct acaatgccgc | 120 |
| catcncttac accatcctca gccaagatcc tgagctccct gacnaaaata tgttcnccat | 180 |
| taacaggaac gcaggagtca tcggtgtggt cnccactggg ctggaccgaa agagtttccc | 240 |
| tacgtgtacc ntggtggttc aagcngctga ccttcanggt gagggttaa tcacnacagc | 300 |
| ancngctgtg atcacagtca ctgntaccaa | 330 |

<210> SEQ ID NO 76
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 76

| gctcgcgcgc ctgcaggtcg acactagtgg atccaaagaa ttcggcacga gaacaacagt | 60 |
| tatctccaag atgctattcg ttgaacccat cctggaggtt tccagcttgc cgacaaccaa | 120 |
| ctcaacaacc aattcagcca ccaaaataac agctaatacc actgatgaac ccaccacaca | 180 |
| acccaccaca gagcccacca cccaacccac catccaaccc acccaaccaa ctacccagct | 240 |
| cccaacagat tctcctaccc agcccactac tgggtccttc tgcccaggac ctgttactct | 300 |
| ctgctctgac ttgganantc attcaacana agccgtgttg ggggaagctt tggtaaattt | 360 |
| ctccctgaag tctctaccacg ccttctc | 387 |

<210> SEQ ID NO 77
<211> LENGTH: 339
<212> TYPE: DNA
<213> ORGANISM: Homo sapien
<220> FEATURE:
<221> NAME/KEY: misc_feature
<222> LOCATION: (1)...(339)
<223> OTHER INFORMATION: n = A,T,C or G

<400> SEQUENCE: 77

| ctgctgatcn gggtcccttt ggagcacaga tgatgcnatg gccancnngg gacaacnacg | 60 |
| tgatctgcgc cctggtcctg gtgtccatnc tggccctcgg nanccctggcc gaggcccana | 120 |

```
canagacgtg tncagtggcc ccccgtgaaa gacagaattg tggttttcct ggtgtcacac      180
cctcccantg tgcaaataag ggctgctgtt tcgacaacac cgttcgtggg gtccctggt       240 gcttctatcc taataccntc nacntcccnc canaaaagga ntgtgaattt tanacacttc      300
tgcagggatc tgcctgcatc ctgacgcngt gccgtcccc                             339
```

```
<210> SEQ ID NO 78
<211> LENGTH: 385
<212> TYPE: DNA
<213> ORGANISM: Homo sapien

<400> SEQUENCE: 78
tcggtcatag ggagagattt gtatgctgta ctatgcagcg tttaaagtta gtgggttttg       60 tgattttttgt attgaatatt gctgtctgtt acaaagtcag ttaaaggtac gttttaatat    120
ttaagttatt ctatcttgga gataaaatct gtatgtgcaa ttcaccggta ttaccagttt    180
attatgtaaa caagagattt ggcatgacat gttctgtatg tttcagggaa aaatgtcttt    240
aatgcttttt caagaactaa cacagttatt cctatactgg attttaggtc tctgaagaac    300
tgctggtgtt taggaataag aatgtgcatg aagcctaaaa taccaagaaa gcttatactg    360
aatttaagca aaaaaaaaaa acccc                                          385
```

```
<210> SEQ ID NO 79
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 79
tcgatacagg gatgtcagag ctgccagaga ctttatcctg aagctttacc aagatcagaa       60
tcctgacaaa gnagaaagtc atctactctc acttcacatg tgctacagat acagacaata    120
ttcgctttgt gtttgctgct gtcaaagaca caattctaca gctaanccta agggaattca    180
accttgtcta aaagctgctg cccactcctc ccctataaca gaagatgtga tttgcaaact    240
ccttgtttta tttgnaagtg cttctgacat cnccagagcc agccccatgc caggaactaa    300
ggatgtc                                                              307
```

```
<210> SEQ ID NO 80
<211> LENGTH: 528
<212> TYPE: DNA
<213> ORGANISM: Homo sapien
<220> FEATURE:
<221> NAME/KEY: misc_feature
<222> LOCATION: (1)...(528)
<223> OTHER INFORMATION: n = A,T,C or G

<400> SEQUENCE: 80
gtcgatacag gaacagcatg tccaaatcga tgtggatgtt tccaagcctg acctcacggc       60
tgccctgcgt gacgtacgtc agcaatatga aagtgtggct gccaagaacc tgcaggaggc    120
agaagaatgg tacaaatcca agtttgctga cctctctgag gctgccaacc ggaacaatga    180
cgccctgcgc caggcaaagc aggagtccac tgagtaccgg agacaggtgc agtccctcac    240
ctgtgaagtg gatgcccctta aaggaaccaa tgagtccctg gaacgccaga tgcgttgaaa    300
tggaagagaa ctttgccgtt gaagctgcta actaccaaga cactattggc cgcctgcagg    360
```

```
atgagattca gaatatgaag ganggaaatg gctcgtcacc ttcgtgaata ccaagacctg    420
ctcaatgtta agatggccct tgacattgaa attgccacct acanggaact gctggangcn    480
aagaaaacca ggatttctct gcctcctccn aactttttcct cccctgaa              528
```

<210> SEQ ID NO 81
<211> LENGTH: 369
<212> TYPE: DNA
<213> ORGANISM: Homo sapien

<400> SEQUENCE: 81

```
agcatggctc ccgaagtttt gccaaaacct cggatgcgtg gccttctggc caggcgtctg     60
cgaaatcata tggctgtagc attcgtgcta tccctggggg ttgcagcttt gtataagttt    120
cgtgtggctg atcaaagaaa gaaggcatac gcagatttct acagaaacta cgatgtcatg    180
aaagattttg aggagatgag gaaggctggt atctttcaga gtgtaaagta atcttggaat    240
ataaagaatt tcttcaggtt gaattaccta gaagtttgtc actgacttgt gttcctgaac    300
tatgacacat gaatatgtgg gctaagaaat agttcctctt gataaataaa caattaacaa    360
aaaaaaaaa                                                           369
```

<210> SEQ ID NO 82
<211> LENGTH: 269
<212> TYPE: DNA
<213> ORGANISM: Homo sapien
<220> FEATURE:
<221> NAME/KEY: misc_feature
<222> LOCATION: (1)...(269)
<223> OTHER INFORMATION: n = A,T,C or G

<400> SEQUENCE: 82

```
atgacaggga tgancaaact tngtctgggg tattgatgaa gatgacctac tgctgatgat     60
accagtgctg ctgtaactga agaaatgcca ccccttgaag gagatgacga cacatcacgc    120
atggaagaag tagactaatc tctggctgag ggatgactta cctgttcagt actctacaat    180
tcctctgata atatattttc aaggatgttt ttctttattt ttgttaatat taaaangtct    240
gtntggnatg acaactnctt taagggggaa                                     269
```

<210> SEQ ID NO 83
<211> LENGTH: 196
<212> TYPE: DNA
<213> ORGANISM: Homo sapien
<220> FEATURE:
<221> NAME/KEY: misc_feature
<222> LOCATION: (1)...(196)
<223> OTHER INFORMATION: n = A,T,C or G

<400> SEQUENCE: 83

```
tttgggtcca attacagcta aagcaaaagt ggttattgaa ctgttttttat cggtctcggg     60 nnttgctaaa ccttcccagg tgtattttgg aggtacagtt gttggcnagc aagctatnaa    120
atctgaagat gaagtgggaa gttnaatana gtatgaatnc agggtaagaa actnaggtaa    180
acctcnaata tncctc                                                    196
```

<210> SEQ ID NO 84
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

```
<400> SEQUENCE: 84
caaacatggg catggtgtca gcgataatgt ttntancagc tcccgacata aatcagtaan        60
tnngatttcc accatatcna ncntcnggaa tttaaccntc aggagnagct cttnntcaga       120
cnccctggaa aaacgagccc cattgnancc anctttgana cataaaacct ggagaaattc       180
tccaatacng aaggtatana gcggggcatc gttgacagca tcacgggtca aaggcttctg       240
gaggctcagg cctgcaaagg tggcatcatc cacccaacca cgggccagaa cctgtcnctt       300
caggacgcag tctcccnggg tgtgattgac caagacatgg ccaccaggct gaagcctgct       360
cagaaagcct tcataggctt cgagggtgtg aagggaaaga agaagatgtc agcagcagag       420
gcagtgaaaa aaaaaaaacc cctatatt                                         448

<210> SEQ ID NO 85
<211> LENGTH: 169
<212> TYPE: DNA
<213> ORGANISM: Homo sapien

<400> SEQUENCE: 85
agcagaccaa ctgccttttg tgagaccttc ccctccctat ccccaacttt aaaggtgtga        60
gagtattagg aaacatgagc agcatatggc ttttgatcag tttttcagtg gcagcatcca       120
atgaacaaga tcctacaagc tgtgcaggca aaacctagca ggaaaaaaa                  169
```